United States Patent [19] [11] 4,050,921
Plant et al. [45] Sept. 27, 1977

[54] REGULATION OF THE NATURAL GROWTH OR DEVELOPMENT OF PLANTS WITH 2-SULFINYL OR 2-SULFONYL PYRIDINE N-OXIDE COMPOUNDS

[75] Inventors: Howard L. Plant, Milford; John W. Zukel, Hamden; Ronald B. Ames, Naugatuck, all of Conn.

[73] Assignee: Uniroyal Inc., New York, N.Y.

[21] Appl. No.: 677,660

[22] Filed: Apr. 16, 1976

[51] Int. Cl.$^2$ .............................................. A01N 9/22
[52] U.S. Cl. ................................ 71/94; 260/294.8 B; 260/294.8 C; 260/294.8 D; 260/294.8 F; 260/294.8 G; 260/294.9; 71/76
[58] Field of Search ...................... 260/294.8 G; 71/94

[56] References Cited
U.S. PATENT DOCUMENTS

| 3,107,994 | 10/1963 | Rawlings et al. | 260/294.8 G |
| 3,155,671 | 11/1964 | D'Amico | 260/294.8 G |
| 3,772,307 | 11/1973 | Kaminsky et al. | 260/294.8 F |

Primary Examiner—Alan L. Rotman
Attorney, Agent, or Firm—James J. Long

[57] ABSTRACT

2-Thio, 2-sulfinyl and 2-sulfonyl pyridine N-oxides of the formula

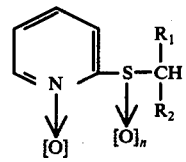

are useful for regulating the natural growth or development of plants. E.g., the compound wherein $n = 1$, $R_1$ = methyl and $R_2$ = 2,3,4-trimethylphenyl retards cotton and increases root growth of turf.

22 Claims, No Drawings

REGULATION OF THE NATURAL GROWTH OR DEVELOPMENT OF PLANTS WITH 2-SULFINYL OR 2-SULFONYL PYRIDINE N-OXIDE COMPOUNDS

This invention relates to a method of regulating the natural growth or development of plants using certain 2-substituted pyridine N-oxides, some of which are believed to be new compounds.

Certain of the compounds employed in the present invention are disclosed as herbicides in commonly assigned copending applications Ser. Nos. 559,188 now U.S. Pat. No. 4,019,893 issued Apr. 26, 1977 and 559,196 (now U.S. Pat. No. 3,960,542 issued June 1, 1976) of Howard L. Plant and Allyn R. Bell, filed Mar. 17, 1975. Other compounds employed herein are disclosed as herbicides in U.S. Pat. Nos. 3,107,994, Rawling et al., Oct. 22, 1963 and 3,155,671, D'Amico, Nov. 3, 1964, or as pharmaceuticals in U.S. Pat. No. 3,772,307, Kaminsky et al., Nov. 13, 1975. However, the non-herbicidal treatment of plants with the presently employed compounds has not heretofore been disclosed, insofar as the present inventors are aware. Certain compounds, to be pointed out hereinbelow, are new chemicals.

In the light of present and future world food problems the necessity to increase productivity in terms of plant efficiency is of paramount importance. Chemical manipulation of plant metabolism to produce desirable results as needed is an effective answer to the situation.

The present invention surprisingly makes it possible to increase the efficiency of photosynthesis by reducing photorespiration. Improvement in yield of major crops such as soybeans, peanuts, cereal grains and cotton can therefore be achieved by more efficient conversion of $CO_2$ into organic compounds by these plants. The method of the invention in general involves regulating the natural growth or development of plants, by applying to said plants an effective plant-regulating amount of a 2-thio-, 2-sulfinyl-, or 2-sulfonyl-pyridine N-oxide of the following formula I:

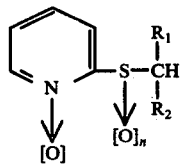

I wherein:
$n$ is 0, 1 or 2;
$R_1$ is hydrogen, alkyl ($C_1$ to $C_{15}$), phenyl or benzyl;
$R_2$ is hydrogen, alkyl ($C_1$ to $C_{12}$), alkenyl ($C_1$ to $C_4$), alkoxycarbonyl ($C_2$ or $C_3$), alicyclic ($C_5$ to $C_6$), phenyl, phenyl substituted with from 1 to 5 substituents which may be the same or different and are selected from the group consisting of lower alkyl ($C_1$ to $C_3$), halogen, cyano, nitro, alkoxy ($C_1$ or $C_2$), phenoxy, dioxymethylene and 2,2-dichlorocyclopropyl; 1-methyl-2,2-dichlorocyclopropyl, 2,2-dichlorocyclopropyl, polycyclic (naphthyl, anthryl), biphenyl, heterocyclic or benzyl;
$R_1$ and $R_2$ may be joined together in the form of a polymethylene chain $-(CH_2)_m-$ where $m$ is 3, 4 or 5 to form a carbocyclic ring;

and when $R_1$ is hydrogen or methyl $R_2$ can be the radical

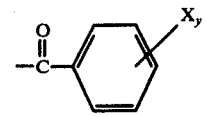

where $y$ is 0, 1 or 2 and the X's are the same or different and are selected from lower alkyl ($C_1$ to $C_3$), halogen, and 2,2-dichlorocyclopropyl.

Certain highly desirable sulfides having the above structure are believed to be new chemical compounds, namely, those of the following formula II:

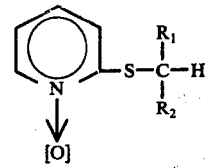

II wherein
$R_1$ is $C_3$ to $C_{15}$ alkyl; and
$R_2$ is 2-naphthyl, phenyl, or phenyl substituted with from 1 to 3 substituents which may be the same or different selected from methyl, chlorine and phenoxy.

The new chemicals of formula II include compounds that are remarkable in certain aspects of their activity.

The compounds employed in this invention, as defined by the above formula, to influence the natural growth or development of plant life have been found to be surprisingly effective plant regulators. It is to be understood that the term "plant regulator" is used herein in its common usage and means a substance which, through physiological action, will accelerate or retard the rate of growth or rate of maturation or otherwise alter the behavior of ornamental or crop plants or the product thereof. Thus, the usage herein conforms to the definitions provided by Congress in Public Law 92-516, the Federal Environmental Pesticide Control Act of 1972, section 2, subsection v, wherein the term "plant regulator" is defined as any substance or mixture of substances intended, through physiological action, for accelerating or retarding the rate of growth or rate of maturation, or for otherwise altering the behavior of plants or the produce thereof, but shall not include substances to the extent that they are intended as plant nutrients, trace elements, nutritional chemicals, plant inoculants, and soil amendments (see also U.S. Pat. No. 3,904,395, Eilrich et al., Sept. 9, 1975).

Thus, in accordance with this invention a method is provided whereby viable plants are treated with a chemical substance which alters their natural growth or development to enhance various agricultural or horticultural features of the plants. As employed herein, the term "natural growth or development" designates the normal life cycle of the plant in accordance with its genetics and its environment, in the absence of artificial, external influences.

The term "active ingredient" will be used hereinafter in this specification to connote one or more of the compounds of the above formula.

It is to be understood that the regulation of natural growth and development does not include killing or herbicidal action. Although phytotoxic or lethal amounts of the active ingredient might be employed to destroy certain plants, it is contemplated here to employ only such amounts of said active ingredient as will serve to regulate the natural growth and development of useful plants without substantial injury. As may be expected, and as long understood by those skilled in the art, such effective plant regulating amounts will vary, not only with the particular active ingredient selected for treatment, but also with the regulatory effect to be achieved, the species of plant being treated and its stage of development, and whether a permanent of transient regulating effect is sought. Other factors which may bear upon the determination of an appropriate plant regulating amount include the plant growth medium, the manner in which the treatment is to be applied, weather conditions such as temperature or rainfall, and the like.

In accordance with the instant invention it has been found that desirable regulation of natural plant growth or development is achieved by application of the active ingredient to plants in various states of development. It will be understood that such expressions as "applying to plants" as used herein include applying to plant parts (e.g., seeds) and extend to indirect application (i.e., applying to soil in which the plant is growing or is to be grown) as well as direct application. Thus, the compounds can advantageously be used as a seed treatment. They can be applied to the soil, and seed or transplants planted in the treated soil, or applied to the plant in the seeding stage, flowering stage or fruiting stage and the like, or can be applied to plants at more than one stage of development. Such application may be made directly to one or more of the plant's parts, such as, stems, leaves, flowers, fruit or the like.

Regulation of the natural growth or development of plants by chemical treatment results from the effect of the chemical substance on the physiological processes of the plant and the effect of such substance may be manifested by the morphology of the plant. As should be readily apparent, said regulation may also result from a combined or sequential effect of the chemical manifesting a response in both physiology and morphology.

In general, regulation of the natural growth or development which leads to a morphological change in the plant is readily noticeable by visual observation. Such changes can be found in the size, shape, color or texture of the treated plant or any of its parts. Similarly, changes in the quantity of plant fruit or flowers can be simply noted.

On the other hand, regulation which leads to changes only in the physiological processes occur within the treated plant and are usually hidden from the eye of an observer. Changes of this type are most often in the production, location, storage or use of naturally occurring chemicals, including hormones, within the plant. Physiological changes in a plant often are recognized when followed by a subsequent change in morphology. Additionally, there are numerous analytical procedures known to those skilled in the art for determining the nature and magnitude of changes in the various physiological processes.

The individual compounds employed in the instant invention serve to regulate the natural growth or development of treated plants in a number of diverse ways and it is to be understood that each compound may not produce identical regulatory effects on each plant species or at every rate of application. As stated above, responses will vary in accordance with the compound, the rate, the plant, etc.

One regulatory response demonstrated by the compounds useful in the practice of this invention can be generally termed retardation of vegetative growth and such a response has a wide variety of beneficial features. In certain plants this retardation of vegetative growth causes a diminution or elimination of apical dominance leading to a shorter main stem and increased lateral branching. This regulation of the natural growth or development of plants produces smaller, bushier plants which often demonstrate increased resistance to climatic extremes, pest infestations and the like. Thus, the method of this invention provides for plants that are in a good state of health and tends to produce more effective plants.

The individual compounds employed in this invention regulate the natural growth or development of treated monocotyledonous and dicotyledonous plants in numerous other and different respects. Included among these other regulatory effects are inducing or preventing axillary bud development. The compounds will also promote the abscission of leaves, flowers and fruits. On cotton such a process has the additional benefit of reducing the potential feeding sites of such important insects as the boll weevil and the pink bollworm by either terminating the growth of the plant or by abscissing young fruiting bodies which are a preferred source of food for insects. Other effects include the alteration of shape of canopy, the delay or acceleration of fruit or pod set, etc. Although regulatory effects such as those described above can be desirable, often it is the ultimate result of these effects upon the economic factor which is of primary significance in crop plants or upon the aesthetic factor in ornamental plants. Thus, it must be recognized that increases in yield of individual plants, increases in the yield per unit of cropping area, improvement in the quality of the plants' product, improvement in the plants' vigor and reductions in the cost of harvesting and/or subsequent processing are all of an individual regulatory effect during the growth or development of a plant. Thus, these compounds promote maturity of some plants. This effect is desirable since earlier harvest can be made. This is especially important for cotton in some areas of the United States and other countries.

The practice of the method of this invention is particularly useful for improving the efficiency of row crops such as soybean (Glycine). The application of the 2-thio-, 2-sulfinyl- or 2-sulfonyl-pyridine N-oxides of the above formula to such growing crop plants reduces the stature of the plants without the expected substantial reduction in seed yield. In this manner the plant's efficiency of production is improved and a means is provided for optimizing the crop by increasing the plant population per unit area and treating said crop with the active ingredient during its growing stage. Such reduction in plant stature also increases accessibility to the field for other treatments, cultivation and harvesting.

The productivity of some plants can be increased by controlling photorespiration. About 5 to 10% of the dry matter of plants comes from the minerals and nitrogen of the soil. The balance or 90 to 95% of the dry weight comes from the conversion of $CO_2$ from the atmosphere by the photosynthetic process. Some plants are efficient converters of $CO_2$ to dry matter, but many such as soybeans, cotton and the cereals are inefficient users of $CO_2$. These plants photorespire or release $CO_2$ under illumination during the daytime. If this loss of $CO_2$ during the daytime is eliminated in soybeans, a theoretical yield increase of 50% is predicted. The present invention makes it possible to reduce photorespiration with a corresponding increase in yield.

In selecting the appropriate non-herbicidal rate of application of the active ingredient, it will be recognized that precise dosages will be dependent upon the plant species being treated, the development stage of the plant, the particular chemical employed, the mode of application (whether to seed, soil, or directly to the plant itself) and various other factors known to those skilled in the art. In general, the active ingredients are applied to seed, soil or to plants at rates of from about 0.05 to about 10 or more pounds per acre. Foliar applications of from 0.1 to 5 pounds of the active ingredient per acre are preferred.

Manifestations of regulant activity include dark foliar color resulting in a darker green plant indicating higher chlorophyll activity (improved rate of photosynthesis), altered canopy, leaf inhibition or abscission, promotion or prevention of axillary bud development, increased pod set, increased tillering, height reduction, promotion of root growth, improved photosynthetic activity by reducing photorespiration.

By way of non-limiting example, Table I below sets forth a number of plant regulant 2-thio-, 2-sulfinyl and 2-sulfonyl-pyridine N-oxides of the above formula I useful in the invention. Methods of preparing such compounds have been described in copending applications Ser. Nos. 559,188 and 559,196 mentioned above (the disclosures of which are hereby incorporated herein by reference) and U.S. Pat. Nos. 3,107,994, 3,155,671 and 3,772,307 mentioned above, as well as Katritsky and Lagouski-Chemistry of Heterocyclic N-oxides, Academic Press (1971) (see also U.S. Pat. Nos. 3,005,852, Freyermuth et al., Oct. 24, 1961, 3,006,962, Schultz et al., Oct. 31, 1961 and 3,006,963, Buc et al., Oct. 31, 1961). The sulfides (i.e., the 2-thiopyridine N-oxides) are commonly prepared from 2-chloropyridine N-oxide with a suitable mercaptan and acid acceptor or conversely the sodium salt of 2-mercaptopyridine N-oxide with a suitable halide. The more biologically active sulfoxides (i.e., the 2-sulfinyl pyridine N-oxides) and sulfones (i.e., the 2-sulfonyl pyridine N-oxides) are prepared in the manner described in the aforementioned applications, Ser. Nos. 559,188 and 559,196. In general, the oxidation of the pyridine N-oxide sulfides to sulfoxides and sulfones is accomplished by employing 30 to 50% hydrogen peroxide in a suitable solvent such as acetic acid or water. The peroxy acids such as peracetic, perbenzoic and metachloroperoxybenzoic work well in solvents varying from chloroform and methylene chloride to glacial acetic acid. When hydrogen peroxide is the oxidant of choice then a metallic acid catalyst such as vanadium, tungsten or molybdenum may be used to advantage but is not essential. Certain sulfides of pyridine can be oxidized directly to the pyridine N-oxide sulfone in a single step. The sulfoxides are not available by this technique. Table I gives the systematic name, melting point (uncorrected, taken on an A. H. Thomas apparatus), empirical formula and analysis for a variety of exemplary 2-thio-, 2-sulfinyl- and 2-sulfonyl pyridine N-oxides useful in the invention; an X mark in the last column of Table I, headed "IR", indicates that the structure was confirmed by infrared spectrographic analysis (using a Perkin Elmer Infracord [trademark]). The numbers assigned to the compounds in Table I are used to identify the compounds in subsequent examples.

TABLE I

| No. | Name | m.p. | Empirical Formula | Analysis Calc/Found | | | | IR |
|---|---|---|---|---|---|---|---|---|
| | | | | C | H | N | S | |
| 1 | 2-(2,2-dichlorocyclopropylmethylsulfinyl)pyridine N-oxide | Oil | $C_9H_9Cl_2NO_2S$ | | | | | X |
| 2 | 2-(phenylmethylthio)pyridine N-oxide | 164–166° | $C_{12}H_{11}NOS$ | | | | | X |
| 3 | 2-(2,2-dichloro-1-methylcyclopropylmethyl-sulfonyl)pyridine N-oxide | 93–95 | $C_{10}H_9Cl_2NO_3S$ | 40.50 / 40.51 | 3.72 / 3.87 | 4.73 / 4.59 | 10.81 / 10.94 | X |
| 4 | 2-(phenylmethylsulfonyl)pyridine N-oxide | 126–128 | $C_{12}H_{11}NO_3S$ | | | | | X |
| 5 | 2-(1-naphthylmethylthiopyridine) N-oxide | 130–133 | $C_{16}H_{13}NOS$ | | | | | X |
| 6 | 2-(3,4-dimetylphenylmethylsulfonyl)pyridine N-oxide | 165–167 | $C_{14}H_{15}NO_3S$ | 60.63 / 60.77 | 5.45 / 5.73 | 5.05 / 5.03 | 11.54 / 11.71 | X |
| 7 | 2-(4-methylphenylmethylsulfonyl)pyridine N-oxide | 149–151 | $C_{13}H_{13}NO_3S$ | | | | | X |
| 8 | 2-(4-chlorophenylmethylsulfonyl)pyridine N-oxide | 154–155 | $C_{12}H_{11}ClNO_3S$ | | | | | X |
| 9 | 2-(1-naphthylmethylsulfonyl)pyridine N-oxide | 183–186 | $C_{13}H_{16}NO_3S$ | | | | | X |
| 10 | 2-(4-chlorophenylmethylthio)pyridine N-oxide | 121–123 | $C_{12}H_{10}ClNOS$ | | | | | X |
| 11 | 2-(4-methylphenylmethylthio)pyridine N-oxide | 121–124 | $C_{13}H_{13}NOS$ | | | | | X |
| 12 | 2-(4-chlorophenylmethylsulfinyl)pyridine N-oxide | 104–107 | $C_{12}H_{10}ClNO_2S$ | | | | | X |
| 13 | 2-(2,5-dimethylphenylmethylthio)pyridine N-oxide | 141–143 | $C_{14}H_{15}NOS$ | | | | | X |
| 14 | 2-(2,5-dimethylphenylmethylsulfonyl)pyridine N-oxide | 156–158 | $C_{14}H_{15}NO_3S$ | 60.63 / 60.66 | 5.45 / 5.56 | 5.05 / 5.18 | 11.54 / 11.81 | X |
| 15 | 2-(4-nitrophenylmethylsulfonyl)pyridine N-oxide | 215–216 | $C_{12}H_{10}N_2O_5S$ | | | | | X |
| 16 | 2-(cyclohexylmethylsulfonyl)pyridine N-oxide | 144–145° | $C_{12}H_{17}NO_3S$ | | | | | X |
| 17 | 2-(2,2-dichlorocyclopropylmethylsulfonyl)pyridine N-oxide | 103–105 | $C_9H_9Cl_2NO_3S$ | | | | | X |
| 18 | 2-(2-ethylphenylmethylthio)pyridine N-oxide | 114–118 | $C_{14}H_{15}NOS$ | | | | | X |
| 19 | 2-(ethylsulfinyl)pyridine N-oxide | 94–96 | $C_7H_9NO_2S$ | | | | | X |
| 20 | 2-(2-benzothiazolylmethylsulfonyl)pyridine N-oxide | 175–176 | $C_{13}H_{10}N_2O_3S_2$ | | | | | X |
| 21 | 2-(2-methylphenylmethylthio)pyridine N-oxide | 134–136 | $C_{13}H_{13}NOS$ | | | | | X |
| 22 | 2-(2-chlorophenylmethylsulfonyl)pyridine N-xodie | 151–152 | $C_{12}H_{10}ClNO_3S$ | | | | | X |
| 23 | 2-(2-chlorophenylmethylthio)pyridine N-oxide | 111–113 | $C_{12}H_{10}ClNOS$ | | | | | X |
| 24 | 2-(dodecylsulfonyl)pyridine N-oxide | 49–51 | $C_{17}H_{29}NO_3S$ | | | | | X |
| 25 | 2-(dodecylthio)pyridine Noxide | 87–89 | $C_{17}H_{29}NOS$ | | | | | X |
| 26 | 2-(1-phenylethylthio)pyridine N-oxide | 112–114 | $C_{13}H_{13}NOS$ | | | | | X |
| 27 | 2-(2-methylphenylmethylsulfonyl)pyridine N-oxide | 159–161 | $C_{13}H_{13}NO_3S$ | 59.31 / 59.30 | 4.93 / 5.21 | 5.32 / 5.31 | | X |
| 28 | 2-(x,y-dichlorophenylmethylsulfonyl)pyridine N-oxide | 132–137 | $C_{12}H_9Cl_2$ | | | | | X |
| 29 | 2-(2,6-dichlorophenylmethylthio)pyridine N-oxide | 240–241 | $C_{12}H_9Cl_2NOS$ | | | | | X |
| 30 | 2-(2,4,6-trimethylphenylmethylthio)pyridine N-oxide | 137–138 | $C_{15}H_{17}NOS$ | | | | | X |
| 31 | 2-(2,4,6-trimethylphenylmethylsulfonyl)pyridine | 173–175 | $C_{15}H_{17}NO_3S$ | 61.90 / 61.97 | 5.84 / 5.06 | 4.81 / 4.79 | | |

TABLE I-continued

| No. | Name | m.p. | Empirical Formula | C (Calc/Found) | H (Calc/Found) | N (Calc/Found) | S | IR |
|---|---|---|---|---|---|---|---|---|
| 32 | 2-(2,6-dichlorophenylmethylsulfonyl)pyridine N-oxide | 214–216 | $C_{12}H_9Cl_2NO_3S$ | 45.37 / 45.67 | 2.83 / 2.89 | 4.40 / 4.55 | | X |
| 33 | 2-([3-trifluoromethylphenyl]methylsulfonyl) pyridine N-oxide | 125–127 | $C_{13}H_{10}F_3NO_3S$ | 49.10 / 48.86 | 3.16 / 2.73 | 4.41 / 4.20 | | X |
| 34 | 2-(2,4-dichlorophenylmethylsulfonyl)pyridine N-oxide | 154–156 | $C_{12}H_9Cl_2NO_3S$ | | | | | X |
| 35 | 2-(1-phenylethylsulfonyl)pyridine N-oxide | 141–143 | $C_{13}H_{13}NO_3S$ | 59.40 / 59.03 | 4.95 / 4.90 | 5.32 / 5.35 | | X |
| 36 | 2-(2,4-dichlorophenylmethylthio)pyridine N-oxide | 173–174 | $C_{12}H_9Cl_2NOS$ | | | | | X |
| 37 | 2-([2-methoxy-5-nitrophenyl]methylsulfonyl) pyridine N-oxide | 226–227 | $C_{13}H_{10}N_2O_6S$ | | | | | X |
| 38 | 2-(3,4-dimethylphenylmethylthio)pyridine N-oxide | 193–195 | $C_{14}H_{15}NOS$ | | | | | X |
| 39 | 2-(isopropylenesulfonyl)pyridine N-oxide | Oil | $C_9H_{11}NO_3S$ | | | | | X |
| 40 | 2-(phenylethylthio)pyridine N-oxide | 118–120 | $C_{13}H_{13}NOS$ | | | | | X |
| 41 | 2-(phenylethylsulfonyl)pyridine N-oxide | 99–100 | $C_{13}H_{13}NO_3S$ | | | | | X |
| 42 | 2-(2,6-dichlorophenylmethylsulfinyl)pyridine N-oxide | 135–137 | $C_{12}H_9Cl_2NO_2S$ | 47.65 / 47.25 | 2.98 / 2.95 | 4.64 / 4.25 | | X |
| 43 | 2-(2-fluorophenylmethylthio)pyridine N-oxide | 135–137 | $C_{12}H_{13}FNOS$ | | | | | X |
| 44 | 2-[(3,4-dioxymethylene-6-chlorophenyl)methyl-sulfonyl]pyridine N-oxide | 179–180 | $C_{13}H_{10}ClNO_5S$ | 47.60 / 46.87 | 3.06 / 2.83 | 4.28 / 4.23 | | X |
| 45 | 2-(2-fluorophenylmethylsulfonyl)pyridine N-oxide | 151–153 | $C_{12}H_{10}FNO_3S$ | 54.00 / 54.03 | 3.74 / 3.79 | 5.24 / 5.32 | | X |
| 46 | 2-(1-ethylpentylsulfonyl)pyridine N-oxide | Oil | $C_{12}H_{19}NO_3S$ | | | | | X |
| 47 | 2-(2-ethylphenylmethylsulfonyl)pyridine N-oxide | – | $C_{14}H_{15}NO_3S$ | | | | | X |
| 48 | 2-(2-hexylsulfonyl)pyridine N-oxide | 71–73 | $C_{12}H_{15}NO_3S$ | | | | | X |
| 49 | 2-(cyclohexylsulfonyl)pyridine N-oxide | 135–138 | $C_{11}H_{15}No_3S$ | | | | | X |
| 50 | 2-(2,5-dimethylphenylmethylsulfinyl)pyridine | 142–144 | $C_{14}H_{15}NO_3S$ | 64.80 / 64.43 | 5.64 / 5.67 | 5.26 / 5.13 | | X |
| 51 | 2-(2-propylthio)pyridine N-oxide | 77–79 | $C_8H_{11}NOS$ | | | | | X |
| 52 | 2-(2-cyanophenylmethylthio)pyridine N-oxide | 154–157 | $C_{13}H_{10}N_2OS$ | | | | | X |
| 53 | 2-(cycloheptylsulfonyl)pyridine N-oxide | 103–107 | $C_{12}H_{17}NO_3S$ | 56.50 / 57.14 | 6.66 / 6.80 | 5.50 / 5.55 | | X |
| 54 | 2-(2-cyanophenylmethylsulfonyl)pyridine N-oxide | 188–190 | $C_{13}H_{10}FN_2O_3S$ | 56.90 / 57.14 | 3.65 / 3.98 | 10.21 / 10.22 | | X |
| 55 | 2-(2-propylsulfonyl)pyridine N-oxide | 110–114 | $C_8H_{11}NO_3S$ | 47.75 / 47.86 | 5.51 / 5.57 | 6.96 / 6.78 | | X |
| 56 | 2-(cycloheptylthio)pyridine N-oxide | 128–131 | $C_{12}H_{17}NOS$ | | | | | X |
| 57 | 2-(2,4-dichlorophenylmethylsulfinyl)pyridine | 138–141 | $C_{12}H_9CL_2NO_2S$ | | | | | X |
| 58 | 2-(phenylethylsulfinyl)pyridine N-oxide | Oil | $C_{13}H_{13}NO_2S$ | | | | | X |
| 59 | 2-[(3-trifluoromethylphenyl)methylsulfinyl]-pyridine N-oxide | 104–108 | $C_{13}N_{10}F_3NO_2S$ | 51.80 / 52.13 | 3.34 / 3.35 | 4.65 / 4.75 | | X |
| 60 | 2-(4-methoxyphenylmethylsulfinyl)pyridine N-oxide | 140–148 | $C_{13}H_{13}NO_3S$ | | | | | X |
| 61 | 2-(phenylmethylsulfinyl)pyridine N-oxide | 119–122 | $C_{12}H_{11}NO_2S$ | | | | | X |
| 62 | 2-(3-methylphenylthio)pyridine N-oxide | 107–109 | $C_{13}H_{13}NOS$ | | | | | X |
| 63 | 2-(3-methylphenylmethylsulfinyl)pyridine N-oxide | 67–71 | $C_{13}H_{13}NO_2S$ | 63.20 / 63.14 | 5.26 / 5.71 | 5.66 / 5.73 | | X |
| 64 | 2-(3-methylphenylmethylsulfonyl)pyridine N-oxide | 171–173 | $C_{13}H_{13}NO_3S$ | | | | | X |
| 65 | 2-(2,4,6-trimethylphenylmethylsulfinyl)pyridine N-oxide | 164–166 | $C_{15}H_{17}NO_2S$ | 65.50 / 66.11 | 6.18 / 6.49 | 5.09 / 5.15 | | X |
| 66 | 2-(2-chlorophenylmethylsulfinyl)pyridine N-oxide | 124–127 | $C_{12}H_{10}ClNO_2S$ | 53.65 / 53.91 | 3.73 / 4.11 | 5.22 / 5.25 | | X |
| 67 | 2-(3,4-dimethylphenylmethylsulfinyl)pyridine N-oxide | 123–126 | $C_{14}H_{15}NO_2S$ | 64.43 / 64.89 | 5.75 / 6.08 | 5.36 / 5.40 | | X |
| 68 | 2-(2-methylphenylmethylsulfinyl)pyridine N-oxide | 99–102 | $C_{13}H_{13}NO_2S$ | 63.14 / 62.66 | 5.30 / 5.31 | 5.66 / 5.45 | | X |
| 69 | 2-(2-cyanophenylmethylsulfinyl)pyridine N-oxide | 158–161 | $C_{13}H_{10}N_2O_2S$ | 60.45 / 69.03 | 3.90 / 3.86 | 10.84 / 10.57 | | X |
| 70 | 2-(4-methylphenylmethylsulfinyl)pyridine N-oxide | 101–103 | $C_{13}H_{13}NO_2S$ | 63.14 / 63.57 | 5.30 / 5.43 | 5.66 / 5.48 | | X |
| 71 | 2-(3-fluorophenylmethylsulfonyl)pyridine N-oxide | 138–140 | $C_{12}H_{10}FNO_3S$ | | | | | X |
| 72 | 2-(4-fluorophenylmethylsulfonyl)pyridine N-oxide | 100–103 | $C_{12}H_{10}FNO_3S$ | | | | | X |
| 73 | 2-(4-fluorophenylmethylsulfinyl)pyridine N-oxide | 136–138 | $C_{12}H_{10}FNO_2S$ | | | | | X |
| 74 | 2-(3-fluorophenylmethylsulfinyl)pyridine N-oxide | 70–74 | $C_{12}H_{10}FNO_2S$ | | | | | X |
| 75 | 2-(2-fluorophenylmethylsulfinyl)pyridine N-oxide | 110–113 | $C_{12}H_{10}FNO_2S$ | 57.40 / 57.43 | 3.98 / 3.95 | 5.57 / 5.68 | | X |
| 76 | 2-(2-oxo-2-phenylethylsulfinyl)pyridine N-oxide | 121–123 | $C_{13}H_{11}NO_3S$ | | | | | X |
| 77 | 2-(2-oxo-2-phenylethylsulfonyl)pyridine N-oxide | 117–120 | $C_{13}H_{11}NO_4S$ | 56.02 / 56.39 | 4.05 / 4.00 | 5.01 / 5.05 | | X |
| 78 | 2-(1-[4-chlorophenyl]ethylthio)pyridine N-oxide | 106–108 | $C_{13}H_{12}ClNOS$ | 58.75 / 58.81 | 4.85 / 5.40 | 5.14 / 5.27 | | X |
| 79 | 2-[1-(4-chlorophenyl)ethylsulfonyl]pyridine N-oxide | 188–191 | $C_{13}H_{12}ClNO_3S$ | | | | | X |
| 80 | 2-(1-phenylbutylthio)pyridine N-oxide | 130–132 | $C_{15}H_{17}NOS$ | 69.48 / 69.48 | 6.51 / 6.61 | 5.46 / 5.40 | | X |
| 81 | 2-(1-[4-methylphenyl]ethylthio)pyridine N-oxide | 83–85 | $C_{14}H_{15}NOS$ | 68.54 / 68.56 | 6.27 / 6.16 | 5.45 / 5.71 | | X |
| 82 | 2-(pentachlorophenylmethylthio)pyridine N-oxide | 183–185 | $C_{12}H_2Cl_5NOS$ | | | | | X |
| 83 | 2-(2,3,6-trichlorophenylmethylthio)pyridine N-oxide | 232–234 | $C_{12}H_8Cl_3NOS$ | | | | | X |
| 84 | 2-(4-cyanophenylmethylthio)pyridine N-oxide | 159–160 | $C_{13}H_{10}N_2OS$ | | | | | X |
| 85 | 2-(2-oxo-2[p-2',2'-dichlorocyclopropylphenyl]-ethylthio)pyridine N-oxide | 163–165 | $C_{16}H_{13}Cl_2NO_2S$ | | | | | X |
| 86 | 2-(2-oxo-2[2,4-dimethylphenyl]ethylthio)pyridine N-oxide | 106–108 | $C_{15}H_{15}NO_2S$ | | | | | X |

TABLE I-continued

| No. | Name | m.p. | Empirical Formula | C | H | N | S | IR |
|---|---|---|---|---|---|---|---|---|
| 87 | 2-(1-[2-naphthyl]ethylthio)pyridine N-oxide | 112–115 | $C_{17}H_{15}NOS$ | 72.94 / 72.58 | 5.35 / 5.37 | 4.98 / 4.98 | | X |
| 88 | 2-(2-methoxy-5-methylphenylmethylsulfonyl)-pyridine N-oxide | 115–118 | $C_{14}H_{15}NO_4S$ | | | | | X |
| 89 | 2-(2-bromo-5-methoxyphenylmethylsulfonyl)pyridine N-oxide | 157–158 | $C_{13}H_{12}BrNO_4S$ | | | | | X |
| 90 | 2-(pentachlorophenylmethylsulfonyl)pyridine N-oxide | 235–238 | $C_{12}H_6Cl_5NO_3S$ | | | | | X |
| 91 | 2-(pentachlorophenylmethylsulfinyl)pyridine N-oxide | 213–215 | $C_{12}H_6Cl_5NO_2S$ | | | | | X |
| 92 | 2-(2,3,6-trichlorophenylmethylsulfonyl)pyridine | 194–196 | $C_{12}H_6Cl_5NO_2S$ | | | | | X |
| 92 | 2-(2,3,6-trichlorophenylmethylsulfonyl)pyridine | 194–196 | $C_{12}H_8Cl_3NO_3S$ | | | | | X |
| 94 | 2-(2,3,6-trichlorophenylmethylsulfinyl)pyridine N-oxide | 168–170 | $C_{12}H_8Cl_3NO_2S$ | 42.82 / 41.89 | 2.39 / 2.32 | 4.16 / 4.18 | | X |
| 95 | 2-(4-cyanophenylmethylsulfonyl)pyridine N-oxide | 215–217 | $C_{13}H_{10}N_2O_3S$ | | | | | X |
| 96 | 2-(4-cyanophenylmethylsulfinyl)pyridine N-oxide | 155–158 | $C_{13}H_{10}N_2O_2S$ | | | | | X |
| 97 | 2-(2-oxo-2-[2,4-dimethylphenyl]ethylsulfonyl) pyridine N-oxide | 149–152 | $C_{15}H_{15}NO_4S$ | | | | | X |
| 98 | 2-(2-oxo-2[2,4-dimethylphenyl]ethylsulfinyl)-pyridine N-oxide | 145–147 | $C_{15}H_{15}NO_3S$ | | | | | X |
| 99 | 2-(1-[2,5-dimethylphenyl]ethylthio)pyridine N-oxide | 118–120 | $C_{15}H_{17}NOS$ | 69.03 / 69.48 | 6.36 / 6.61 | 5.21 / 5.40 | | X |
| 100 | 2-(1-[4-bromophenyl]ethylthio)pyridine N-oxide | 113–115 | $C_{13}H_{12}BrNOS$ | 50.20 / 50.35 | 4.16 / 3.90 | 4.45 / 4.52 | | X |
| 101 | 2-(2,5-diisopropylphenylmethylsulfonyl)pyridine N-oxide | 120–123 | $C_{18}H_{23}NO_3S$ | 64.84 / 64.10 | 6.95 / 6.89 | 4.20 / 4.31 | | X |
| 102 | 2-(2,5-diisopropylphenylmethylsulfinyl)pyridine N-oxide | 83–86 | $C_{18}H_{23}NO_2S$ | | | | | X |
| 103 | 2-(2-oxo-2[p-2',2'-dichlorocyclopropylphenyl]-ethylsulfonyl)pyridine N-oxide | 96–99 | $C_{16}H_{13}Cl_2NO_3S$ | 51.94 / 51.90 | 3.45 / 3.54 | 3.91 / 3.78 | | X |
| 104 | 2-(1-phenylbutylsulfonyl)pyridine N-oxide | 145–148 | $C_{15}H_{17}NO_3S$ | 61.83 / 61.53 | 5.88 / 5.85 | 4.89 / 4.95 | | X |
| 105 | 2-[1-(4-methylphenyl)ethylsulfonyl]pyridine N-oxide | 158–160 | $C_{14}H_{15}NO_3S$ | 60.35 / 61.18 | 5.45 / 5.70 | 5.05 / 5.22 | | X |
| 106 | 2-[1-(4-methylphenyl)ethylsulfinyl]pyridine N-oxide | 121–123 | $C_{14}H_{15}NO_2S$ | | | | | X |
| 107 | 2-[1-(2-thienyl)ethylsulfonyl]pyridine N-oxide | 147–149 | $C_{11}H_{11}NO_3S_2$ | 49.05 / 48.90 | 4.12 / 4.39 | 5.20 / 5.21 | | x |
| 108 | 2-[1-(4-fluorophenyl)ethylsulfoyl]pyridine N-oxide | 142–144 | $C_{13}H_{12}FNO_3S$ | 55.50 / 55.47 | 4.30 / 4.61 | 4.98 / 5.07 | | X |
| 109 | 2-[1-(2,5-dimethylphenyl)ethylsulfonyl]pyridine N-oxide | 160–163 | $C_{15}H_{17}NO_3S$ | | | | | X |
| 110 | 2-(1-phenylpropylthio)pyridine N-oxide | 158–160 | $C_{14}H_{15}NOS$ | 68.51 / 68.56 | 6.07 / 6.16 | 5.52 / 5.71 | | X |
| 111 | 2-(1-[3,4-dichlorophenyl]ethylthiopyridine N-oxide | Oil | $C_{13}H_{11}Cl_2NOS$ | 52.11 / 52.05 | 3.31 / 3.67 | 4.94 / 4.67 | | X |
| 112 | 2-(3,4-dioxymethylenephenylmethylthio)pyridine N-oxide | 146–148 | $C_{13}H_{11}NO_3S$ | | | | | X |
| 113 | 2-[1-(4-fluorophenyl)ethylsulfinyl]pyridine N-oxide | 98–101 | $C_{13}H_{12}FNO_2S$ | 58.85 / 54.94 | 4.56 / 5.08 | 5.28 / 5.34 | | X |
| 114 | 2-[1-(2-naphthyl)ethylsulfonyl]pyridine N-oxide | 144–146 | $C_{17}H_{15}NO_3$ | | | | | X |
| 115 | 2-(1-[2,5-dimethylphenyl]octylthio)pyridine N-oxide | 92–94 | $C_{21}H_{29}NOS$ | 73.42 / 73.44 | 7.91 / 8.51 | 4.18 / 4.08 | | X |
| 116 | 2-[1-(4-bromophenyl)ethylsulfinyl]pyridine N-oxide | 177–180 | $C_{13}H_{12}BrNO_2S$ | | | | | X |
| 117 | 2-[1-(4-brommophenyl)ethylsulfonyl]pyridine N-oxide | 193–195 | $C_{13}H_{12}BrNO_3S$ | 45.63 / 45.04 | 3.45 / 3.32 | 4.09 / 4.15 | | X |
| 118 | 2-(1-phenylpropylsulfonyl)pyridine N-oxide | 144–146 | $C_{14}H_{15}NO_3S$ | 60.63 / 60.57 | 5.45 / 5.39 | 5.05 / 5.11 | | X |
| 119 | 2-(2-oxo-2-[2,5-dimethylphenyl]ethylthio)-pyridine N-oxide | 63–66 | $C_{15}H_{15}NO_2S$ | 65.90 / 65.91 | 6.01 / 5.53 | 4.51 / 5.13 | | X |
| 120 | 2-(2-oxo-2-[4-fluorophenyl]ethylsulfinyl)pyridine N-oxide | 150–152 | $C_{13}H_{10}FNO_3S$ | | | | | X |
| 121 | 2-83,4-dichlorophenylmethylsulfinyl)pyridine N-oxide | 133–135 | $C_{12}H_9Cl_2NO_2S$ | 47.70 / 47.44 | 3.00 / 2.92 | 4.64 / 4.71 | | X |
| 122 | 2-(1-[2,5-dimethylphenyl]dodecylthio)pyridine N-oxide | 90–92 | $C_{25}H_{37}NOS$ | 75.19 / 75.15 | 9.45 / 9.33 | 3.39 / 3.51 | | X |
| 123 | 2-83-bromophenylmethylthio)pyridine N-oxide | 132–134 | $C_{12}H_{10}BrNOS$ | | | | | X |
| 124 | 2-(3-bromophenylmethylsulfonyl)pyridine N-oxide | 145–147 | $C_{12}H_{10}BrNO_3S$ | | | | | X |
| 125 | 2-(3-bromophenylmethylsulfinyl)pyridine N-oxide | 155 | $C_{12}H_{10}BrNO_2S$ | | | | | X |
| 126 | 2-(1-[3,4-dichlorophenyl]ethylsulfonyl)pyridine N-oxide | 129–134 | $C_3H_{11}Cl_2NO_3S$ | | | | | X |
| 127 | 2-(2-oxo-2-[2,5-dimethylphenyl]ethylsulfonyl)-pyridine N-oxide | 142–144 | $C_{15}H_{15}NO_4S$ | | | | | X |
| 128 | 2-(2-oxo-2-[2,5-dimethylphenyl]ethylsulfinyl)-pyridine N-oxide | 153–155 | $C_{15}H_{15}NO_3S$ | | | | | X |
| 129 | 2-(3,4-methylenedioxyphenylmethylsulfinyl)-pyridine N-oxide | 171–173 | $C_{13}H_{11}NO_4S$ | | | | | X |

TABLE I-continued

| No. | Name | m.p. | Empirical Formula | Analysis Calc/Found C | H | N | S | IR |
|---|---|---|---|---|---|---|---|---|
| 130 | 2-83,4-methylenedioxyphenylmethylsulfoyl)-pyridine N-oxide | 163-165 | $C_{13}H_{10}NO_5S$ | | | | | X |
| 131 | 2-(2-oxo-2-[2,5-diisopropylphenyl]ethylsulfinyl)-pyridine N-oxide | 116-118 | $C_{19}H_{23}NO_3S$ | | | | | X |
| 132 | 2-(2-pyridylsulfonyl)propionic acid ethyl ester | 109-110 | $C_{10}H_{13}NO_5S$ | | | | | X |
| 133 | 2-(2-oxo-2-phenyl-1-methylethylsulfinyl)pyridine N-oxide | 120-124 | $C_{14}H_{13}NO_3S$ | | | | | X |
| 134 | 2-(2-oxo-2-phenyl)-1-methylethylsulfonyl)pyridine N-oxide | 179-182 | $C_{14}H_{13}NO_4S$ | | | | | X |
| 135 | 2-(1-[2,3,6-trimethylphenyl]ethylthio)pyridine N-oxide | 108-110 | $C_{15}H_{17}NOS$ | | | | | X |
| 136 | 2-(2-nitrophenylmethylthio)pyridine N-oxide | 120-123 | $C_{12}H_{10}N_2O_3S$ | | | | | X |
| 137 | 2-(4-[2,2-dichlorocyclopropyl]phenylmethylthio)-pyridine N-oxide | 122-127 | $C_{15}H_{13}Cl_2NOS$ | | | | | X |
| 138 | 2-(2,3,6-trimethylphenylmethylsulfonyl)pyridine N-oxide | 155 | $C_{15}H_{17}NO_3S$ | | | | | X |
| 139 | 2-(1-[2,4,6-trimethylphenyl]ethylsulfonyl)-pyridine N-oxide | 172-175 | $C_{16}H_{19}NO_3S$ | | | | | X |
| 140 | 2-(2-nitrophenylmethylsulfoyl)pyridine N-oxide | 155-158 | $C_{12}H_{11}N_2O_5S$ | | | | | X |
| 141 | 2-(2-nitrophenylmethylsulfinyl)pyridine N-oxide | 165-167 | $C_{12}H_{11}N_2O_3S$ | | | | | X |
| 142 | 2-(2,3,6-trimethylphenylmethylsulfinyl)pyridin N-oxide | 72-75 | $C_{15}H_{18}NO_2S$ | | | | | X |
| 143 | 2-(2-methyl-1-naphthylmethylsulfonyl)pyridine N-oxide | 195-198 | $C_{17}H_{17}NO_3S$ | | | | | X |
| 144 | 2-(2-methyl-1-naphthylmethylsulfinyl)pyridine N-oxide | 122-125 | $C_{17}H_{15}NO_2S$ | | | | | X |
| 145 | 2-(α-[2-methylphenyl]phenylmethylsulfonyl)pyridine N-oxide | 122-25 | $C_{19}H_{17}NO_2S$ | 67.24 / 66.52 | 5.05 / 5.29 | 4.13 / 4.13 | | X |
| 146 | 2-(2-iodophenylmethylsulfonyl)pyridine N-oxide | 142-146 | $C_{12}H_{11}INO_3S$ | | | | | X |
| 147 | 2-(2-iodophenylmethylsulfinyl)pyridine N-oxide | 160-163 | $C_{12}H_{11}INO_2S$ | | | | | X |
| 148 | 2-(1-[4-nitrophenyl]ethylsulfonyl)pyridine N-oxide | 167-171 | $C_{13}H_{12}N_2O_5S$ | | | | | X |
| 149 | 2-(4-[2,2-dichloropropyl]phenylmethylsulfonyl)pyridine N-oxide | oil | $C_{15}H_{13}Cl_2NO_3S$ | | | | | X |
| 150 | 2-(4-[2,2-dichlorocyclopropyl]phenylmethylsulfinyl)pyridine N-oxide | oil | $C_{15}H_{13}Cl_2NO_2S$ | | | | | X |
| 151 | 2-(1-[1-naphthyl]ethylsulfonyl)pyridine N-oxide | wax | $C_{17}H_{15}NO_3S$ | | | | | X |
| 152 | 2-[1-(1-naphthyl)ethylsulfinyl]pyridine N-oxide | 127-130 | $C_{17}H_{15}NO_2S$ | | | | | X |
| 153 | 2-(3,4-dimethoxyphenylmethylthio)pyridine N-oxide | 141-143 | $C_{14}H:hd 15NO_3S$ | 60.73 / 60.5 | 5.49 / 5.45 | 5.23 / 5.05 | | X |
| 154 | 2-(3,4-dimethoxyphenylmethylsulfinyl)pyridine N-oxide | 133-135 | $C_{14}H_{15}NO_4S$ | | | | | X |
| 155 | 2-(3,4-dimethoxyphenylmethylsulfonyl)pyridine N-oxide | 159-161 | $C_{14}H_{15}NO_5S$ | | | | | X |
| 156 | 2-(1-[2,5-diethylphenyl]ethylsulfonyl)pyridine N-oxide | 124-127 | $C_{17}H_{21}NO_3S$ | | | | | X |
| 157 | 2-(1-[2,5-diisopropylphenyl]ethylthio)pyridine N-oxide | 124-126 | $C_{19}H_{25}NOS$ | 72.33 / 72.35 | 7.75 / 7.99 | 4.54 / 4.44 | | X |
| 158 | 2-(cyclopentylsulfinyl)pyridine N-oxide | 80-82 | $C_{10}H_{13}NO_2S$ | | | | | X |
| 159 | 2-(cyclopentylsulfonyl)pyridine N-oxide | 107-109 | $C_{10}H_{13}NO_3S$ | | | | | X |
| 160 | 2-(2,5-dimethoxyphenylmethylsulfoyl)pyridine N-oxide | 129-132 | $C_{14}H_{15}NO_5S$ | | | | | X |
| 161 | 2-(2,5-dimethoxyphenylmethylsulfinyl)pyridine N-oxide | 136-138 | $C_{14}H_{15}NO_4S$ | | | | | X |
| 162 | 2-(2-ethoxyphenylmethylsulfinyl)pyridine N-oxide | 135-138 | $C_{14}H_{15}NO_3S$ | | | | | X |
| 163 | 2-(2-ethoxyphenylmethylsulfonyl)pyridine N-oxide | 145-147 | $C_{14}H_{15}NO_4S$ | | | | | X |
| 164 | 2-1-[2-chloro-4-methylphenyl]ethylthio)-pyridine N-oxide | 118-120 | $C_{14}H_{14}ClNOS$ | 60.06 / 60.04 | 4.98 / 5.65 | 5.21 / 5.00 | | X |
| 165 | 2-(1-[2-chloro-4-methylphenyl]ethylsulfonyl)-pyridine N-oxide | 166-168 | $C_{14}H_{14}ClNO_3S$ | 53.89 / 54.00 | 4.50 / 4.53 | 4.48 / 4.49 | | X |
| 166 | 2-(1-[2-chloro-4-methylphenyl]ethylsulfinyl)-pyridine N-oxide | 121-123 | $C_{14}H_{14}CNO_2S$ | 56.74 / 56.91 | 4.77 / 4.77 | 4.82 / 4.74 | | X |
| 167 | 2-(1-[2-chloro-5-methylphenyl]ethylthio0-pyridine N-oxide | 112-114 | $C_{14}H_{14}ClNOS$ | 60.5 / 60.04 | 5.13 / 5.65 | 5.17 / 5.00 | | X |
| 168 | 2-(1-[2,5-diisopropylphenyl]ethylsulfonyl)-pyridine N-oxide | 123-127 | $C_{19}H_{25}NO_3S$ | | | | | X |
| 169 | 2-(2,3,5,6-tetrachloro-4-methylphenylmethylthio)-pyridine N-oxide | 178-180 | $C_{13}H_9Cl_4NOS$ | | | | | X |
| 170 | 2-(2,3,5,6-tetrachloro-4-methylphenylmethylsulfinyl)pyridine N-oxide | 204-205 | $C_{13}H_9Cl_4NO_2S$ | | | | | X |
| 171 | 2-(2,3,5,6-tetrachloro-4-methylphenylmethylsulfonyl)pyridine N-oxide | 215-218 | $C_{13}H_9Cl_4NO_3S$ | | | | | X |
| 172 | 2-(1-[2,5-dichlorophenyl]ethylthio)pyridine N-oxide | 145-147 | $C_{13}H_{11}Cl_2NOS$ | 52.11 / 52.01 | 3.70 / 3.69 | 4.54 / 4.67 | | X |
| 173 | 2-(1-[2-chloro-5-methylphenyl]ethylsulfinyl)-pyridine N-oxide | 125-127 | $C_{14}H_{14}ClNO_2S$ | 57.65 / 56.91 | 4.92 / 4.77 | 4.71 / 4.74 | | X |
| 174 | 2-(1-[2-chloro-5-methylphenyl]ethylsulfonyl)-pyridine N-oxide | 175-177 | $C_{14}H_{14}ClNO_3S$ | 54.00 / 54.00 | 4.77 / 4.53 | 4.42 / 4.49 | | X |

TABLE I-continued

| No. | Name | m.p. | Empirical Formula | Analysis Calc/Found C | H | N | S | IR |
|---|---|---|---|---|---|---|---|---|
| 175 | 2-(1-[2,5-dichlorophenyl]ethylsulfinyl)pyridine N-oxide | 127–128 | $C_{13}H_{11}Cl_2NO_2S$ | 49.36 / 49.36 | 3.56 / 3.51 | 4.37 / 4.43 | | X |
| 176 | 2-(1-[2,5-dichlorophenyl]ethylsulfonyl)pyridine N-oxide | 158–160 | $C_{13}H_{11}Cl_2NO_3S$ | 47.00 / 47.00 | 3.46 / 3.34 | 4.17 / 4.22 | | X |
| 177 | 2-(-1[2,4,5-trimethylphenyl]ethylsulfinyl)-pyridine N-oxide | 134–137 | $C_{16}H_{19}NO_2$ | | | | | X |
| 178 | 2-(1-[2,4,5-trimethylphenyl]ethylsulfonyl)-pyridine N-oxide | 132–134 | $C_{16}H_{19}NO_3S$ | | | | | X |
| 179 | 2-(1-[2,3,4-trimethylphenyl]ethylsulfinyl)-pyridine N-oxide | 164–167 | $C_{16}H_{19}NO_2S$ | | | | | X |
| 180 | 2-(1-[2,3,4-trimethylphenyl]ethylsulfonyl)-pyridine N-oxide | 155–158 | $C_{16}H_{19}NO_3S$ | | | | | X |
| 181 | 2-(1-[2,3,4,5-tetramethylphenyl]ethylsulfinyl)-pyridine N-oxide | 185–190 | $C_{17}H_{21}NO_2S$ | | | | | X |
| 182 | 2-(1-[2,3,4,5-tetramethylphenyl]ethylsulfonyl)-pyridine N-oxide | 145–150 | $C_{17}H_{21}NO_3S$ | | | | | X |
| 183 | 2-(3,4,5-trimethoxyphenylmethylsulfinyl)-pyridine N-oxide | 144–146 | $C_{15}H_{17}NO_5S$ | 55.28 / 55.73 | 5.25 / 5.30 | 4.26 / 4.33 | | X |
| 184 | 2-(3,4,5-trimethoxyphenylmethylsulfonyl)-pyridine N-oxide | 153–155 | $C_{15}H_{17}NO_6S$ | 53.09 / 53.10 | 4.95 / 5.05 | 4.10 / 4.13 | | X |
| 185 | 2-(9-anthranylmethylsulfinyl)pyridine N-oxide | 150–153 | $C_{20}H_{15}NO_2S$ | | | | | X |
| 186 | 2-(2-thienylmethylthio)pyridine N-oxide | 166–170 | $C_{10}H_9NOS_2$ | | | | | X |
| 187 | 2-(2-thienylmethylsulfinyl)pyridine N-oxide | 115–119 | $C_{10}H_9NO_2S_2$ | | | | | X |
| 188 | 2-(2-thienylmethylsulfonyl)pyridine N-oxide | 90–97 | $C_{10}H_9NO_3S_2$ | | | | | X |
| 189 | 2-(1-phenylethylsulfinyl)pyridine N-oxide | 130–131 | $C_{13}H_{13}NO_2S$ | | | | | X |
| 190 | 2-(1-[2,5-dimethylphenyl]ethylsulfinyl)pyridine N-oxide | 126–127 | $C_{15}H_{17}NO_2S$ | | | | | X |
| 191 | 2-(1-[4-chlorophenyl]ethylsulfinyl)pyridine N-oxide | 130–131 | $C_{13}H_{12}ClNO_2S$ | | | | | X |
| 192 | 2-(1-[2,4-dichloro-3-methyl]ethylsulfonyl)pyridine N-oxide | 192–194 | $C_{14}H_{13}Cl_2NO_3S$ | | | | | X |
| 193 | 2-(1-[2,4-dichloro-3-methylphenyl]ethylsulfinyl)pyridine N-oxide | 147–148 | $C_{14}H_{13}Cl_2NO_2S$ | | | | | X |
| 194 | 2-(1-phenyl-2-propylthio)pyridine N-oxide | 125–127 | $C_{14}H_{15}NOS$ | | | | | X |
| 195 | 2-(3-methyl-1-[2,5-dimethylphenyl]butylsulfonyl)pyridine N-oxide | 185–187 | $C_{18}H_{23}NO_3S$ | | | | | X |
| 196 | 2-(1-phenyl-2-propylsulfonyl)pyridine N-oxide | 99–10 | $C_{14}H_{15}NO_3S$ | | | | | X |
| 197 | 2-(1-phenyl-2-propylsulfinyl)pyridine N-oxide | Oil | $C_{14}H_{15}NO_2S$ | | | | | X |
| 198 | 2-(1-[2,5-dichlorothienyl-3-]ethylthio)pyridine N-oxide | 129–133 | $C_{11}H_9Cl_2NOS_2$ | | | | | X |
| 199 | 2-(1-[(2,5-dimethylphenyl]-2-phenylethylthio)-pyridine N-oxide | Oil | $C_{21}H_{21}NOS$ | | | | | X |
| 200 | 2-(4-vinylphenylmethylthio)pyridine N-oxide | 103–105 | $C_{14}H_{13}NOS$ | | | | | X |
| 201 | 2-(4-vinylphenylmethylsulfinyl)pyridine N-oxide | Oil | $C_{14}H_{13}NO_2S$ | | | | | X |
| 202 | 2-(4-biphenylmethylthio)pyridine N-oxide | 130–132 | $C_{19}H_{17}NOS$ | | | | | X |
| 203 | 2-(1-[4-phenoxyphenyl]ethylthio)pyridine N-oxide | Oil | $C_{19}H_{17}NO_2S$ | | | | | X |
| 204 | 2-(1-[4-phenoxyphenyl]ethylsulfoyl)pyridine N-oxide | Oil | $C_{19}H_{17}NO_4S$ | | | | | X |
| 205 | 2-(2-methyl-5-isopropylphenylmethylthio)pyridine N-oxide | Oil | $C_{17}H_{21}NOS$ | | | | | X |
| 206 | 2-(2-methyl-5-isopropylphenylmethylsulfonyl)-pyridine N-oxide | Oil | $C_{17}H_{21}NO_3S$ | | | | | X |
| 207 | 2-(1-[5-indanyl]ethylthio)pyridine N-oxide | Oil | $C_{16}H_{17}NOS$ | | | | | X |
| 208 | 2-(1-[5-indanyl]ethylsulfonyl)pyridine N-oxide | 138–140 | $C_{16}H_{17}NO_3S$ | | | | | X |
| 209 | 2-(3-methyl-1-[2,5-dimethylphenyl]butylthio)-pyridine N-oxide | Oil | $C_{18}H_{23}NOS$ | | | | | X |
| 210 | 2-(1-[2,5-dimethylphenyl]butylthio)pyridine N-oxide | Oil | $C_{17}H_{21}ONS$ | | | | | X |
| 212 | 2-[1-(p-chlorophenyl)octylthio]pyridine N-oxide | 71–73 | $C_{19}H_{24}ClNOS$ | | | | | X |
| 213 | 2-[1-(p-chlorophenyl)butylthio]pyridine N-oxide | 52–54 | $C_{15}H_{16}ClNOS$ | | | | | X |
| 214 | 2-[1-(p-chlorophenyl)dodecylthio]pyridine N-oxide | 69–71 | $C_{23}H_{32}ClNOS$ | | | | | X |
| 215 | 2-[1-(2-chloro-5-methylphenyl)octylthio]-pyridine N-oxide | 102–104 | $C_{20}H_{26}ClNOS$ | 66.02 / 66.77 | 7.21 / 7.28 | 3.85 / 3.75 | 8.80 / 8.86 | X |
| 217 | 2-[1-(2-naphthalene)octylthio]pyridine N-oxide | 75–76 | $C_{23}H_{27}NOS$ | 75.611 / 74.63 | 7.45 / 7.34 | 3.83 / 3.78 | 8.76 / 8.54 | X |
| 217 | 2-[1-(4-phenoxyphenyl)octylthio]pyridine N-oxide | 91–92 | $C_{25}H_{29}NO_2S$ | 73.71 / 72.77 | 7.12 / 7.03 | 3.43 / 3.87 | 7.86 / 7.68 | X |
| 218 | 2-[1-(3,4,5-trimethylphenyl)octylthio]-pyridine N-oxide | Oil | $C_{22}H_{31}NOS$ | | | | | X |
| 219 | 2-[1-(4-chlorophenyl)hexadecylthio]pyridine N-oxide | 65–66 | $C_{27}H_{40}ClNOS$ | 70.20 / 71.29 | 8.66 / 9.10 | 3.03 / 2.77 | 6.93 / 6.09 | X |
| 220 | 2-[1-(2,5-dimethylphenyl)hexadecylthio]-pyridine N-oxide | 81–83 | $C_{29}H_{45}NOS$ | 76.50 / 76.72 | 9.96 / 9.83 | 3.07 / 3.06 | 7.02 / 6.64 | X |

The following preparations illustrate methods of making typical compounds of Table I.

Compound 80

2-(1-Phenylbutylthio)pyridine N-oxide

A mixture of 16.9 gms (0.1 mol) of 1-phenylbutylchloride, 36 gms of a 40% aqueous solution of the sodium salt of 2-mercaptopyridine N-oxide (0.1 mol) and 50 ml of ethanol was warmed and stirred at 50° to 60° C. for 2.5 hours. The cooled reaction mixture was poured into 500 ml of water with agitation. The precipitated product was filtered, washed with water and dried. After recrystallization for ethanol a yield of 10 gms (45% theory) of white crystals was obtained.

Melting point 130°–132° C.

Analysis based on $C_{15}H_{17}NOS$—Calc: C 69.48; H 6.61; N 5.40. Found: C 69.48; H 6.51; N 5.46.

Compound 139

2-(1-[2,4,6-Trimethylphenyl]ethylsulfonyl)pryridine N-oxide

To a vigorously stirred mixture of 5.6 gm (0.02 mol) of 2-(1-[2,4,6-trimethylphenyl]ethylthio)pyridine N-oxide in 50 ml of chloroform and 50 ml of phosphate buffer solution (pH 7.5) maintained at 0° to 5° C. is slowly added 8 gm (0.04 mol) metachloroperoxybenzoic acid (85%) (MCPBA) in 100 ml of chloroform. After addition is completed the temperature is allowed to become ambient. Stirring is continued for 16 hours.

The chloroform layer is separated, washed with sodium bicarbonate solution to remove the benzoic acid and dried over sodium sulfate. Removal of the chloroform yields on oil which crystallized upon standing. Recrystallization from ethanol yields 3 gms (50% theory) or product.

Melting point 172° – 175° C.

IR: $SO_2$ 1310, 1140; NO 1270, 845 cm$^{-1}$.

Compound 68

2-(2-Methylphenylmethysulfinyl)pyridine N-oxide

To a vigorously stirred solution of 6.9 gm (0.03 mol) of 2-(2-methylphenylmethylthio)pyridine N-oxide in 50 ml of chloroform maintained at 0° to 10° C. is slowly added a solution of 6 gm (0.03 mol) MCPBA (85%) in 100 ml of chloroform. When addition is complete the temperature is allowed to rise to ambient. After sixteen hours the reaction solution is washed up in the manner described in Example 139.

The resultant residual oil crystallizes upon standing and after recrystallizing from ethanol, 4.7 gm (58% theory) of product is obtained.

Melting point 99°–102° C.

Analysis based on $C_{13}H_{13}NO_2S$—Calc: C 63.14; H 5.30; N 5.66. Found: C 62.66; H 5.31; N 5.45.

Compound 140

2-(2-Nitrophenylmethylsulfonyl)pyridine N-oxide

The procedure employed is identical to that of Example 139 using 5.2 gm (0.02 mol) 2-(2-nitrophenylmethylthio)pyridine N-oxide in 50 ml chloroform with 5 gms (0.04 mol) MCPBA in 100 ml chloroform.

The crude product which is only sparingly soluble in hot ethanol required 300 ml for recrystallization to yield 5 gms (96% theory) of product.

Melting point 155°–158° C.

IR: $SO_2$ 1330, 1140; NO 1280, 845 cm$^{-1}$.

Compound 115

2-(2-[2,5-Dimethylphenyl]octylthio)pyridine N-oxide

A mixture of 24 gm (0.1 mol) of 1-(2,5-dimethylphenyl)n-hexylchloride and 36 gms of a 40% aqueous solution of the sodium salt of 2-mercaptopyridine N-oxide in 50 ml of ethanol is heated with stirring at 60° to 70° for 1 hour. The ethanol is removed under vacuum and the residual slurry extracted with two 75 ml portions of chloroform. The chloroform solution is dried over sodium sulfate, filtered and evaporated to approximately 30 gms of crude material. Recrystallization from ethyl acetate yields 23 gm (68% theory) of pure product.

Melting point 92°–94° C.

IR: NO 1255, 840; > 4CH$_2$ chain 710 cm$^{-1}$.

Compound 75

2-(2-Fluorophenylmethylsulfinyl)pyridine N-oxide

The procedure employed is identical to that of Example 68 using 5.7 gm (0.024 mol) 2-(2-fluorophenylmethylthio)pyridine N-oxide in 50 ml of chloroform with 4.8 gm (0.024 mol) MCPBA in 75 ml chloroform.

The residual crude oil crystallizes upon standing and after recrystallization from ethanol yields 3.8 gm (65% theory) of product.

Melting point 110°–113° C.

Analysis based on $C_{12}H_{11}FNO_2S$—Calc: C 57.36; H 4.01; N 5.58. Found: C 57.43; H 3.95; N 5.68.

Compound 96

2-(4-Cyanophenylmethylsulfinyl)pyridine N-oxide

The procedure employed is identical to that of Example 68 using 3.6 gm (0.015 mol) 2-(4-cyanophenylmethylthio)pyridine N-oxide in 50 ml of chloroform with 3 gm (0.015 mol) MCPBA in 50 ml chloroform.

The crude product is recrystallized from ethanol to yield 215 gm (66% theory) of product.

Melting point 155°–158° C.

IR: NO 1240, 840; SO 1045 cm$^{-1}$.

Compound 50

2-(2,5-Dimethylphenylmethylsulfinyl)pyridine N-oxide

A vigorously stirred slurry consisting of 30 gm (0.12 mol) 2-(2,5-dimethylphenylthio)pyridine N-oxide in 130 ml of 5% aqueous acetic acid and 0.3 gm of vanadium pentoxide is brought to 80° C. and 12 gm (0.12 mol) of 30% hydrogen peroxide added slowly. The addition is exothermic necessitating some intermittent cooling to maintain the temperature below 85° C. The addition requires about fifteen minutes during which time the slurry changes to a homogeneous solution. The reaction mixture is cooled down precipitating the solid sulfoxide. Filtration followed by water wash and drying yielded 30 gm (96% theory) of product.

Melting point 145°–147° C.

Analysis based on $C_{14}H_{15}NO_2S$—Calc. C 64.34; H 5.75; N 5.36. Found: C 64.43; H 5.67; N 5.13.

Compound 62

2-(3,4-Dimethylphenylmethylsulfinyl)pyridine N-oxide

The procedure employed is identical to that of Example 68 using 7.4 gm (0.03 mol) 2-(3,4-dimethylphenylmethylthio)pyridine N-oxide in 50 ml of chloroform with 6 gm (0.03 mol) MCPBA (85%) in 100 ml chloroform.

The crude product is recrystallized from ethanol to yield 5.7 gm (75% theory) of product.

Melting point 123°–126° C.

Analysis based on $C_{14}H_{15}NO_2S$—Calc: C 64.34; H 5.75; N 5.36. Found: C 64.89; H 6.08; N 5.50.

Compound 128

2-(2-Oxo-2-[2,5-dimethylphenyl]ethylsulfinyl)pyridine N-oxide

The procedure employed is identical to that of Example 68 using 8.2 gm (0.03 mol) 2-(2-oxo-2-[2,5-dimethylphenyl]ethylthio)pyridine N-oxide in 50 ml chloroform with 6 gm (0.03 mol) MCPBA (85%) in 100 ml chloroform.

The crude product is recrystallized from ethanol to yield 5.4 gm (64% theory) of product.

Melting point 153°-155° C. (decomp.).

IR: C = 0 1680, NO 1240, 845, SO 1055, 1075 (doublet) cm$^{-1}$.

Compound 6

2-(3,4-Dimethylphenylmethylsulfonyl)pyridine N-oxide

Twenty ml (0.2 mol) of 30% hydrogen peroxide is added slowly and with stirring to 11.5 gm (0.05 mol) of 2-(3,4-dimethylphenylmethylthio)pyridine in 50 ml of glacial acetic acid maintained at ambient temperature. After 1 hour the mixture is gradually heated to 80°-85° C. and maintained for 10 hours. Cool and add an equal volume of water. The volume is reduced by one-half by evaporation. When peroxide is detected in the residue with starch iodide paper the dilution and evaporation procedure is repeated, until the peroxide has been removed. Evaporation is then carried to a residual oil which is taken up in 7:3 chloroform:acetone and chromatographed on a silica gel column.

5.5 gms of product is isolated and recrystallized from ethanol (40% theory).

Melting point 165°-167° C.

Analysis based on $C_{14}H_{15}NO_3S$—Calc: C 60.63; H 5.41; N 5.03; S 11.55. Found: C 60.77; H 5.73; N 4.98; S 11.73.

Compound 57

2-(2,4-Dichlorophenylmethylsulfinyl)pyridine N-oxide

The procedure employed is identical to that of Example 68 using 5.8 gm (0.02 mol) 2-(2,4-Dichlorophenylmethylthio)pyridine N-oxide in 50 ml of chloroform and 4 gm (0.02 mol) MCPBA in 100 ml of chloroform.

The crude material is recrystallized from ethanol to yield 5.5 gm (90% theory) of pure product.

Melting point 138°-141° C.

IR Bands NO 1240, 838 CM$^{-1}$, SO 1050 cm$^{-1}$.

Compound 138

2-(2,3,6-Trimethylphenylmethylsulfonyl)pyridine N-oxide

The procedure employed is identical to that of Example 139 using 10.4 gm (0.04 mol) 2-(2,3,6-trimethylphenylmethylthio)pyridine N-oxide in 50 ml of chloroform and 16 gm (0.08 mol) MCPBA in 200 ml of chloroform.

The oily residue from the work-up crystallizes and is recrystallized from ethanol to give 7.9 gm (69% theory) of pure product.

Melting point 152°-155° C.

Analysis based on $C_{15}H_{17}NO_3S$—Calc: C 61.83; H 5.88; N 4.81. Found: C 61.28; H 5.87; N 4.92.

Compound 63

2-(3-Methylphenylmethylsulfinyl)pyridine N-oxide

The procedure employed is identical with that of Example 68 using 4.6 gm (0.02 mol) 2-(3-Methylphenyl-methylthio)pyridine N-oxide in 50 ml of chloroform and 4 gm (0.02 mol) MCPBA in 100 ml chloroform.

Crude material is recrystallized from ethylacetate to give 2 gm (45% theory) of pure product.

Melting point 67°-71° C.

Analysis based on $C_{13}H_{13}NO_2S$—Calc: C 63.20; H 5.26; N 5.66. Found: C 63.14; H 5.71; N 5.73.

Compound 60

2-(4-Methoxyphenylmethylsulfinyl)pyridine N-oxide

The procedure employed is identical to that of Example 68 using 7 gm (0.028 mol) 2-(4-methoxyphenylmethylthio)pyridine N-oxide in 50 ml of chloroform and 5.6 gm (0.028 mol) MCPBA in 100 ml chloroform.

The crude material is recrystallized from ethanol to give 6 gm (82% theory) of pure product.

Melting point 140°-143° C.

IR Bands NO 1250, 835 cm$^{-1}$, SO 1040.

Compound 121

2-(3,4-dichlorophenylmethylsulfinyl)pyridine N-oxide

The procedure employed is identical to that of Example 68 using 8 gm (0.028 mol) 2-(3,4-dichlorophenylmethylthio)pyridine N-oxide in 50 ml of chloroform and 5.6 gm (0.028 mol) MCPBA in 100 ml chloroform.

The crude material is recrystallized from ethanol to give 5.6 gm (82% theory) of pure product.

Melting point 133°-135° C.

Analysis based on $C_{12}H_9Cl_2NO_2S$—Calc: C 47.70; H 3.00; N 4.64. Found: C 47.44; H 2.92; N 4.71.

Compound 58

2-(2-Phenylethylsulfinyl)pyridine N-oxide

The procedure employed is identical to that of Example 68 using 2.8 gm (0.012 mol) 2-(2-phenylethylthio)pyridine N-oxide in 25 ml of chloroform with 2.4 gm (0.012 mol) MCPBA in 50 ml chloroform.

The product is an oil and purity is determined by TLC. Structure is verified by IR.

Significant Bands NO 1250, 845 cm$^{-1}$, SO 1050 cm$^{-1}$, 5 ArCH 750, 695 cm$^{-1}$.

Compound 122

2-(1-[2,5-Dimethylphenyl]dodecylthio)pyridine N-oxide

A mixture of 46.2 gm (0.15 mol) of 1-phenyldodecyl-chloride, 54 gms of a 40% aqueous solution of the sodium salt of 2-mercaptopyridine N-oxide (0.15 mol) and 100 ml of ethanol was warmed to 60° with stirring for a period of 2 hours. The cooled reaction mixture was poured into 600 ml water with agitation. The precipitated solid was filtered, washed with water and dried. Recrystallization from ethyl acetate yielded 30 gms (50% theory) of white crystalline product.

Melting point 90°-92° C.

Analysis based on $C_{25}H_{37}NOS$—Calc: C 75.15; H 9.33; N 3.51. Found: C 75.19; H 9.45; N 3.56.

Surprisingly the 2-thio, 2-sulfinyl and 2-sulfonyl pyridine N-oxides disclosed herein have novel and variable plant regulating properties. Through coordination of the proper mode of application, dosage and timing the compounds of this series give such varying responses as growth stimulation, growth retardation and increased productivity.

Particularly interesting retardant and stimulation responses to the application of these compounds include the following areas:

Turf

The maintenance of grasses normally employed for functional and esthetic purposes about homes, factories and highways includes regular mowing. For highway and commercial upkeep and the service represents a considerable cost factor and to the homeowner a necessary nuisance; at times the turf may turn brown temporarily and unwanted root retardation results. To date turf control has been attained to a certain degree with maleic hydrazide but pronounced browning of the tops and unwanted root retardation result. The compounds employed in this invention show unique properties in that the turf top growth is retarded without losing the desirable greenness, and root growth in many cases actually shows enhancement yielding a healthier sod.

The turf species of interest include Manhattan rye grass, Jamestown chewings fescue, Colonial bent, Kingston bent, Bermuda, Baron bluegrass and St. Augustine.

Preferred pyridine N-oxide derivatives which can be employed as turf retardants in accordance with the invention include:

| No. | |
|---|---|
| 109* | 2-(1-[2,5-dimethylphenyl]ethylsulfonyl)pyridine N-oxide |
| 35* | 2-(1-phenylethylsulfonyl)pyridine N-oxide |
| 105 | 2-(1-[4-methylphenyl]ethylsulfonyl)pyridine N-oxide |
| 42 | 2-(2,6-dichlorophenylmethylsulfinyl)pyridine N-oxide |
| 139** | 2-(1-[2,4,6-trimethylphenyl]ethylsulfonyl)-pyridine N-oxide |
| 31 | 2-(2,4,6-trimethylphenylmethylsulfonyl)pyridine N-oxide |
| 79 | 2-(1-[4-chlorophenyl]ethylsulfonyl)pyridine N-oxide |
| 14 | 2-(2,5-dimethylphenylmethylsulfonyl)pyridine N-oxide |
| 57 | 2-(2,4-dichlorophenylmethylsulfinyl)pyridine N-oxide |
| 138 | 2-(2,3,6-trimethylphenylmethylsulfonyl)pyridine N-oxide |
| 6 | 2-(3,4-dimethylphenylmethylsulfonyl)pyridine N-oxide |
| 68** | 2-(2-methylphenylmethylsulfinyl)pyridine N-oxide |
| 27 | 2-(2-methylphenylmethylsulfonyl)pyridine N-oxide |
| 142 | 2-(2,3,6-trimethylphenylmethylsulfinyl)pyridine N-oxide |
| 128 | 2-(2-oxo-[2,5-dimethylphenyl]ethylsulfinyl)-pyridine N-oxide |

*most preferred
**root stimulant — top retardant

The turf retardants described herein are highly active on the variety of turf grasses when applied in dosages of 0.125 to 8 pounds per acre. The compounds may be formulated as liquid or impregnated granule for easy application or in any of a number of other forms as known to the art. The formulations may contain more than one of the described pyridine N-oxide derivatives, other active retardants or synergists.

Cereal Grains

The dual response to retardation and stimulation is of value on cereal grains (particularly wheat, as well as barley, rye, oats, rice, etc.) to produce a shorter plant with a larger number of seed heads per plant by promoting increased tillering. The overall results are to reduce possibility for lodging with increased productivity.

Preferred 2-pyridine N-oxide derivatives which can be employed as plant regulators on wheat or other cereal grains in accordance with the invention include:

| No. | |
|---|---|
| 14 | 2-(2,5-dimethylphenylmethylsulfonyl)pyridine N-oxide |
| 6 | 2-(3,4-dimethylphenylmethylsulfonyl)pyridine N-oxide |
| 109 | 2-(1-[2,5-dimethylphenyl]ethylsulfonyl)pyridine N-oxide |

Sugar Producing Species

Increase in productivity of sugar producing species, such as sugar beets and sugar cane, is a valuable aspect of the invention. Thus, for example, it has been demonstrated that treatment of sugar beets with the claimed compounds results in increased beet weight. To exemplify this, sugar beets were planted in the field at Bethany, Connecticut. 2-(2,6-Dichlorophenylmethylsulfinyl)pyridine N-oxide (Compound 42) was applied as a soil treatment at 4 and 8 pounds per acre at the end of July when the beets were about half grown. About 1 month later the effect of the treatment on photorespiration was determined by enclosing a large leaf of a plant in a plastic chamber, impermeable to $CO_2$. Air was aspirated from the chamber at intervals and the $CO_2$ level determined by infra red absorption of the gas. At equilibrium the beets treated with the compound at 4 pounds per acre reduced the $CO_2$ level by 35% when compared to the untreated control exposed to the same conditions. The $CO_2$ level at 8 pounds per acre was reduced by 36% when compared to the control. At harvest there was a yield increase of 8 and 12% at 4 and 8 pounds per acre respectively, when compared to the controls.

Preferred 2-pyridine N-oxides employed as a beet root stimulant in accordance with the invention include:

| No. | |
|---|---|
| 42* | 2-(2,6-dichlorophenylmethylsulfinyl)pyridine N-oxide |
| 68 | 2-(2-methylphenylmethylsulfinyl)pyridine N-oxide |
| 131 | 2-(2-oxo-2-[2,5-diisopropylphenyl]ethylsulfinyl)-pyridine N-oxide |
| 140 | 2-(2-nitrophenylmethylsulfonyl)pyridine N-oxide |
| 115* | 2-(1-[2,5-dimethylphenyl]octylthio)pyridine N-oxide |
| 122 | 2-(1-[2,5-dimethylphenyl]dodecylthio)pyridine N-oxide |

*most preferred

Legumes

The employment of the compounds of this invention on soybeans and other legumes such as beans, peanuts, alfalfa and clover, makes it possible to increase the efficiency of the plant and thereby vastly increase productivity. This is accomplished without altering the normal growth significantly. To exemplify this the Corsoy variety of soybeans was planted in the field at Bethany, Connecticut. When the plants had completed setting of pods, 2-(1-phenylethylsulfonyl)-pyridine N-oxide (Compound 35) was sprayed at 2000 parts per million to wet the foliage. About one month later one of the plants in the treated plot was enclosed in a plastic which is not permeable to $CO_2$. Air was aspirated from the plastic chamber at intervals and the $CO_2$ level determined by infra red absorption of the gas. At equilibrium the $CO_2$ level was reduced by 45% when compared to an untreated control plant. This reduction in photorespiration was accompanied by an increase in yield of the harvested soybeans by 6.0%.

Preferred 2-pyridine N-oxides which can thus be employed as productivity enhancers in accordance with the invention include:

| No. | |
|---|---|
| 35* | 2-(1-phenylethylsulfonyl)pyridine N-oxide |
| 42* | 2-(2,6-dichlorophenylmethylsulfinyl)pyridine N-oxide |
| 75 | 2-(2-fluorophenylmethylsulfinyl)pyridine N-oxide |
| 68 | 2-(2-methylphenylmethylsulfinyl)pyridine N-oxide |
| 27 | 2-(2-methylphenylmethylsulfonyl)pyridine N-oxide |
| 96 | 2-(4-cyanophenylmethylsulfinyl)pyridine N-oxide |
| 57* | 2-(2,4-dichlorophenylmethylsulfinyl)pyridine N-oxide |
| 83* | 2-(2,3,6-trichlorophenylmethylthio)pyridine N-oxide |
| 50* | 2-(2,5-dimethylphenylmethylsulfinyl)pyridine N-oxide |
| 67 | 2-(3,4-dimethylphenylmethylsulfinyl)pyridine N-oxide |
| 79 | 2-(1-[4-chlorophenyl]ethylsulfonyl)pyridine N-oxide |
| 114 | 2-(1-[2-naphthyl]ethylsulfonyl)pyridine N-oxide |
| 128 | 2-(2-oxo-2-[2,5-dimethylphenyl]ethylsulfinyl)-pyridine N-oxide |
| 2 | 2-(phenylmethylthio)pyridine N-oxide |

*most preferred

Cotton

In order to facilitate mechanical harvesting it is desirable to reduce the height of the cotton plant to decrease the possibility of lodging. The action of the compounds of this invention, when employed as a foliar spray, terminates apical growth. This termination of growth, once the desired number of bolls has formed, prevents the formation and setting of additional bolls which never mature resulting in lower crop yields.

Field test have shown that 2-(2,6-dichlorophenylmethylsulfinyl)pyridine N-oxide (Compound 42), for example, terminates growth of cotton, promotes maturity of the bolls for earlier harvest and causes young squares to abscise. These are the preferred feeding sites of the boll weevil and pink bollworm, hence their elimination reduces the desirability of this plant for these insects.

High rates promoted abscission of the leaves and prevented regrowth of the axillary buds. This response is desirable for mechanical harvesting of the mature cotton.

Productivity of plants or the production of dry weight per unit of ground area is primarily determined by the total $CO_2$ assimilated during photosynthesis, minus the $CO_2$ released as photorespiration. The invention makes it possible to markedly reduce photorespiration, hence improve productivity of plants. Productivity by the following plants can be improved: vegetables such as lettuce, beans, spinach; cereals such as wheat, oats, barley, rice; tobacco, hay grasses, sugar beets, cotton and sunflower.

Promotion of inhibition of axillary buds growth can be useful for control of suckers on tabacco, prevention of sprouting of root crops such as potatoes, beets and carrots.

The promotion of abscission can be useful as a harvest aid for cotton, the mechanical harvesting of fruits such as citrus and cherries.

The promotion of tillering and reduction of height of grain can be useful in prevention of lodging and increasing yield of oats, barley, rye and rice.

The promotion of root growth can increase yields of such underground root crops as beets, carrots and potatoes.

Preferred pyridine N-oxide derivatives which can thus be employed as growth terminators in accordance with the invention include:

| No. | |
|---|---|
| 61 | 2-(phenylmethylsulfinyl)pyridine N-oxide |
| 63 | 2-(3-methylphenylmethylsulfinyl)pyridine N-oxide |
| 10 | 2-(4-chlorophenylmethylthio)pyridine N-oxide |
| 60 | 2-(4-methoxyphenylmethylsulfinyl)pyridine N-oxide |
| 42* | 2-(2,6-dichlorophenylmethylsulfinyl)pyridine N-oxide |
| 121 | 2-(3,4-dichlorophenylmethylsulfinyl)pyridine N-oxide |
| 109 | 2-(1-[2,5-dimethylphenyl]ethylsulfonyl)pyridine N-oxide |
| 83 | 2-(2,3,6-trichlorophenylmethylthio)pyridine N-oxide |
| 58 | 2-(2-phenylethylsulfinyl)pyridine N-oxide |

*most preferred

Formulations of the compounds for use in this invention can be prepared in conventional ways. They include dusts, granules, pellets, solutions, suspensions, emulsions, wettable powders, emulsifiable concentrates, oil suspensions, dispersions to include flowable formulations, for example the active ingredient suspended either in oil or water. Formulations also include slow release compositions as a part of any of the following procedures and also include encapsulation of the active ingredient. Many of these may be applied directly to the seed, soil or to the plants. Sprayable formulations can be extended in suitable media and used at spray volumes of from a few pints to several hundred gallons per acre. High strength concentrates are primarily used as intermediates for further formulation. The formulations, broadly, contain about 0.5 to 99% by weight of active ingredient(s) and at least one of (a) about 0.1 to 50% surfactant(s) and (b) about 0.5 to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–89 | 1–10 |
| Oil Suspensions, Emulsions, Solutions (including Emulsifiable concentrates) | 5–50 | 40–95 | 0–50 |
| Aqueous Suspensions | 10–50 | 40–90 | 1–50 |
| Dusts | 1–25 | 70–99 | 0–5 |
| Granules and Pellets | 1–95 | 5–99 | 0–15 |
| High Strength Concentrates | 90–100 | 0–10 | 0–5 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing. Lower concentrations of active ingredient can aid in accurate application at the very low rates reached for this invention. Sprayable and dust formulations are preferred.

Typical solid diluents are described in Watkins, et al., "Handbook of Insecticide Dust Diluents and Carriers", 2nd Ed., Dorland Books, Caldwell, N. J. The more absorptive diluents are preferred for wettable powders and the denser ones for dusts. Typical liquid diluents and solvents are described in Marsden, "Solvents Guide", second edition, Interscience, New York, 1950. Solubility under 0.5% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co. Inc., New York, 1964, list surfactants and recommended uses. All formulations can contain minor amount of additives to reduce foam, caking, corrosion, microbiological growth, etc.

The methods of making such formulations are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084) or by blending liquids, inert ingredients and previously ground dry active ingredients, followed by a dispersion cycle. Granules and pellets may be made by spraying the active material upon preformed granular carriers or by agglomeration techniques. See J. E. Browning, "Agglomeration", Chemical Engineering, December 4, 1967, pp. 147 ff. and "Perry's Chemical Engineer's Handbook", 4th Ed., McGraw-Hill, N. Y., 1963, pp. 8-59 ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, Line 43 through Col. 7, line 62 and Ex. 8, 12, 15, 39, 41, 52, 53, 58, 132, 138-140, 162-164, 166, 167, 169-182.

H. Gysin and E. Knusli, U.S. Pat. No. 2,891,855, June 23, 1959, Col, 3, Line 66 through Col. 5, Line 17 and Examples 1-4.

G. C. Klingmah, "Weed Control as a Science", John Wiley and Sons, Inc., New York, 1961 pp. 81-96.

J. D. Fryer and S. A. Evans, "Weed Control Handbook", fifth edition Blackwell Scientific Publications, Oxford, 1968, pp. 101-103.

Typical formulations are shown in the following examples. All percentages are by weight.

Formulation A

| Formulation A | |
|---|---|
| Wettable Powder | Percent |
| Compound 16 | 40 |
| dioctyl sodium sulfosuccinate | 1.5 |
| sodium ligninsulfonate | 3 |
| low viscosity methyl cellulose | 1.5 |
| attapulgite clay | 54 |

Thoroughly blend the ingredients then pass through an air mill to produce an average particle size under 15 microns. Reblend and sift through a U.S.S. No. 50 sieve (0.3 mm opening) before packaging.

All compounds of the invention may be formulated in the same manner.

Formulation B

| Formulation B | |
|---|---|
| High Strength Concentrate | Percent |
| Compound 42 | 98.5 |
| silica aerogel | 0.5 |
| synthetic amorphous fine silica | 1.0 |

Blend and grind the ingredients in a hammer mill to produce a high strength concentrate essentially all passing a U.S.S. sieve (0.3 mm openings). This material may then be formulated in a variety of ways.

Formulation C

| Formulation C | |
|---|---|
| Dust | Percent |
| high strength concentrate formulation B | 25.4 |
| pyrophyilite powdered | 74.6 |

Thoroughly blend the ingredients and package for use.

Formulation D

| Formulation D | |
|---|---|
| Aqueous Suspension | Percent |
| Compound 139 | 25 |
| hydrated attapulgite clay | 3 |
| crude calcium ligninsulfonate | 10 |
| sodium dihydrogen phosphate | 0.5 |
| water | 61.5 |

Grind the ingredients together in a sand mill until the solid particles have been reduced to diameters under 10 microns.

Formulation E

| Formulation E | |
|---|---|
| Oil Suspension | Percent |
| Compound 184 | 25 |
| polyoxyethylene sorbitol hexaoleate | 5 |
| highly aliphatic hydrocarbon oil | 70 |

Grind the ingredients together in a sand mill until the solid particles have been reduced to under about 5 microns. The resulting thick suspension may be applied directly, but preferably after being extended with oils or emulsified in water.

Illustrative plant regulant responses for typical 2-thio, 2-sulfinyl and 2-sulfonyl pyridine N-oxides of the formula stated above are shown in Table II, where plant regulant responses are indicated by the symbols defined at the beginning of Table II.

TABLE II

Plant Regulators

RW = retards wheat >30% 6000 ppm
RT = retards turf >50%/8.5#/A
RC = retards cotton >30%
RS = retards soybeans >30%
STR = stimulates turf roots >25%
SSB = stimulates sugar beets >25%
WT = wheat tillering
P = enhances production of soybeans >50%

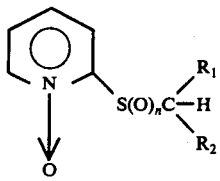

| No. | n | $R_1$ | $R_2$ | Activity |
|---|---|---|---|---|
| 1 | 1 | H | 2,2-dichlorocyclopropyl | RT, RC |
| 2 | 0 | H | phenyl | P, RC |
| 3 | 2 | H | 1-methyl-2,2-dichlorocyclopropyl | RC |
| 4 | 2 | H | phenyl | RT |
| 5 | 0 | H | 1-naphthyl | RT |
| 6 | 2 | H | 3,4-dimethylphenyl | RT, WT |
| 7 | 2 | H | 4-methylphenyl | RT |
| 8 | 2 | H | 4-chlorophenyl | RT |
| 9 | 2 | H | 1-naphthyl | RT, RW |
| 10 | 0 | H | 4-chlorophenyl | RC |
| 11 | 0 | H | 4-methylphenyl | RC |
| 12 | 1 | H | 4-chlorophenyl | RT, RC |
| 13 | 0 | H | 2,5-dimethylphenyl | RT |
| 14 | 2 | H | 2,5-dimethylphenyl | RT, RW |
| 15 | 2 | H | 4-nitrophenyl | RS |
| 16 | 2 | H | cyclohexyl | RS |
| 17 | 2 | H | 2,2-dichlorocyclopropyl | RT |
| 18 | 0 | H | 2-ethylphenyl | RT |
| 19 | 1 | H | methyl | RW |
| 20 | 2 | H | 2-benzothiazole | RS |
| 21 | 0 | H | 2-methylphenyl | RT, RS |
| 22 | 2 | H | 2-chlorophenyl | RT |
| 23 | 0 | H | 2-chlorophenyl | RT |
| 24 | 2 | H | n-undecyl | RC |
| 25 | 0 | H | n-decyl | RS |
| 26 | 0 | $CH_3$ | phenyl | RS |
| 27 | 2 | H | 2-methylphenyl | STR, RT, P, RS |
| 28 | 2 | H | x, y-dichlorophenyl | RT |
| 29 | 0 | H | 2,6-dichlorophenyl | RT |
| 30 | 0 | H | 2,4,6-trimethylphenyl | RT |
| 31 | 2 | H | 2,4,6-trimethylphenyl | RT, P, RW |
| 32 | 2 | H | 2,6-dichlorophenyl | RT, RW |
| 33 | 2 | H | 3-trifluoromethylphenyl | RW |
| 34 | 2 | H | 2,4-dichlorophenyl | RW |
| 35 | 2 | $CH_3$ | phenyl | STR, RT |
| 36 | 0 | H | 2,4-dichlorophenyl | RT |
| 37 | 2 | H | 2-methoxy-5-nitrophenyl | RT |
| 38 | 0 | H | 3,4-dimethylphenyl | RT |
| 39 | 2 | H | isopropenyl | RT |
| 40 | 0 | H | benzyl | RT |
| 41 | 2 | H | benzyl | RT |
| 42 | 1 | H | 2,6-dichlorophenyl | RT, RW, RS |
| 43 | 0 | H | 2-fluorophenyl | RT, RC, RW |
| 44 | 2 | H | 2-chloro-3,4-dioxymethylene | P, RW |
| 45 | 2 | H | 2-fluorophenyl | RT, RW |
| 46 | 2 | ethyl | n-butyl | RT, RC |
| 47 | 2 | H | 2-ethylphenyl | RT, RW |
| 48 | 2 | methyl | n-butyl | RT |
| 49 | 2 | cyclohexyl | | RT |
| 50 | 1 | H | 2,5-dimethylphenyl | RT, P, RW |
| 51 | 0 | methyl | methyl | RT |
| 52 | 0 | H | 2-cyanophenyl | RS |
| 53 | 2 | cycloheptyl | | RW |
| 54 | 2 | H | 2-cyanophenyl | RT |
| 55 | 2 | methyl | methyl | RT |
| 56 | 0 | cycloheptyl | | RT |
| 57 | 1 | H | 2,4-dichlorophenyl | RT, P, RS, RW |
| 58 | 1 | H | benzyl | RC, RW, RS |
| 59 | 1 | H | 3-trifluoromethylphenyl | RT, RC, RS |
| 60 | 1 | H | 4-methoxyphenyl | RT, RC |
| 61 | 1 | H | phenyl | RT, RS |
| 62 | 0 | H | 3-methylphenyl | RT, RS |
| 63 | 1 | H | 3-methylphenyl | RT, RC, RS |

TABLE II-continued
Plant Regulators

RW = retards wheat >30% 6000 ppm  
RT = retards turf >50%/8.5#/A  
RC = retards cotton >30%  
RS = retards soybeans >30%  
STR = stimulates turf roots >25%  
SSB = stimulates sugar beets >25%  
WT = wheat tillering  
P = enhances production of soybeans >50%

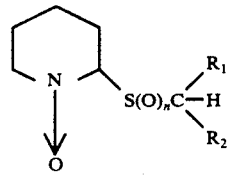

| No. | n | $R_1$ | $R_2$ | Activity |
|---|---|---|---|---|
| 64 | 2 | H | 3-methylphenyl | RT, P, RS, RW |
| 65 | 1 | H | 2,4,6-trimethylphenyl | RT, P, RW, RS |
| 66 | 1 | H | 2-chlorophenyl | RT, RS |
| 67 | 1 | H | 3,4-dimethylphenyl | RT, P, RW, RS |
| 68 | 1 | H | 2-methylphenyl | STR, RT, SSB, RS |
| 69 | 1 | H | 2-cyanophenyl | STR, RT, RS, RW |
| 70 | 1 | H | 4-methylphenyl | RT, RS |
| 71 | 2 | H | 3-fluorophenyl | RT, RC |
| 72 | 1 | H | 4-fluorophenyl | RT, RS, RW, RC |
| 73 | 2 | H | 4-fluorophenyl | RT, RC |
| 74 | 1 | H | 3-fluorophenyl | RT, RS, RW |
| 75 | 1 | H | 2-fluorophenyl | RT, P, RS |
| 76 | 1 | H | oxophenyl | RT, RW |
| 77 | 2 | H | oxophenyl | RS |
| 78 | 0 | methyl | 4-chlorophenyl | RS |
| 79 | 2 | methyl | 4-chlorophenyl | STR, RT, P, RS, RW |
| 80 | 0 | propyl | phenyl | P, RC, RS |
| 81 | 0 | methyl | 4-methylphenyl | RC |
| 82 | 0 | H | pentachlorophenyl | RC |
| 83 | 0 | H | 2,3,6-trichlorophenyl | RT, P, RC, RW |
| 84 | 0 | H | 4-cyanophenyl | RT, P |
| 85 | 0 | H | oxo-4-(2,2-dichlorocyclopropyl)phenyl | RT |
| 86 | 0 | H | oxo-2,4-dimethylphenyl | RT |
| 87 | 0 | methyl | 2-naphthyl | RT, RS |
| 88 | 2 | H | 2-methoxy-5-methylphenyl | RT, RS, RW |
| 89 | 2 | H | 2-bromo-5-methoxyphenyl | RT, RS, RW |
| 90 | 2 | H | pentachlorophenyl | RS, RW |
| 91 | 1 | H | pentachlorophenyl | RT, RS, RW |
| 92 | 2 | H | 2,3,6-trichlorophenyl | RT, RS, RW |
| 94 | 1 | H | 2,3,6-trichlorophenyl | RT |
| 95 | 2 | H | 4-cyanophenyl | RT, RW |
| 96 | 1 | H | 4-cyanophenyl | RT, P |
| 97 | 2 | H | oxo-2,4-dimethylphenyl | RT, RW |
| 98 | 1 | H | oxo-2,4-dimethylphenyl | RT, RW, RS |
| 99 | 0 | methyl | 2,5-dimethylphenyl | P, RW, RS |
| 100 | 0 | methyl | 4-bromophenyl | RW |
| 101 | 2 | H | 2,5-diisopropylphenyl | RW |
| 102 | 1 | H | 2,5-diisopropylphenyl | STR, RT, RW |
| 103 | 1 | H | oxo-4-(2,2-dichlorocyclopropyl)phenyl | RS |
| 104 | 2 | propyl | phenyl | RS, RW |
| 105 | 2 | methyl | 4-methylphenyl | RT, RS, RC, RS |
| 106 | 2 | methyl | 4-methylphenyl | RT |
| 107 | 2 | methyl | 2-thienyl | RW, RS |
| 108 | 2 | methyl | 4-fluorophenyl | RT, RW, RS, RC |
| 109 | 2 | methyl | 2,5-dimethylphenyl | RT, RC, RW, RS, WT |
| 110 | 0 | ethyl | phenyl | RS, RW |
| 111 | 0 | methyl | 3,4-dichlorohenyl | RC |
| 112 | 0 | H | 3,4-dioxymethylenephenyl | RC |
| 113 | 1 | methyl | 4-fluorophenyl | RC, RS, RW |
| 114 | 2 | methyl | 2-naphthyl | STR, RT, P |
| 115 | 0 | n-heptyl | 2,5-dimethylphenyl | STR, RT, SSB |
| 116 | 1 | methyl | 4-bromophenyl | RS, RC |
| 117 | 2 | methyl | 4-bromophenyl | RW, RS, RC |
| 118 | 2 | ethyl | phenyl | RC, RS |
| 119 | 0 | H | oxo-2,5-dimethylphenyl | P |
| 120 | 1 | H | oxo-4-fluorophenyl | RW, RC |
| 121 | 1 | H | 3,4-dichlorophenyl | RC, RS, RW |

TABLE II-continued
Plant Regulators

RW = retards wheat >30% 6000 ppm
RT = retards turf >50%/8.5#/A
RC = retards cotton >30%
RS = retards soybeans >30%
STR = stimulates turf roots >25%
SSB = stimulates sugar beets >25%
WT = wheat tillering
P = enhances production of soybeans >50%

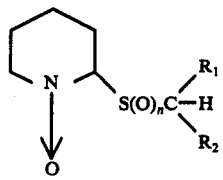

| No. | n | $R_1$ | $R_2$ | Activity |
|---|---|---|---|---|
| 122 | 0 | n-undecyl | 2,5-dimethylphenyl | SSB, RW |
| 123 | 0 | H | 3-bromophenyl | P, RC, RW |
| 124 | 2 | H | 3-bromophenyl | STR, RT |
| 125 | 1 | H | 3-bromophenyl | STR, RT, RC, RW, RS |
| 126 | 2 | methyl | 3,4-dichlorophenyl | STR, RT |
| 127 | 2 | H | oxo-2,5-dimethyl-phenyl | RT, RC, RW |
| 128 | 1 | H | oxo-2,5-dimethyl-phenyl | RT, P, RC, RS, RW |
| 129 | 1 | H | 3,4-dioxymethylene-phenyl | RT, RC, RS, RW |
| 130 | 2 | H | 3,4-dioxymethylene-phenyl | STR, RT, RC, RS, RW |
| 131 | 1 | H | oxo-2,5-diosopropyl-phenyl | STR, RT, SSB, RC |
| 132 | 2 | H | 2-propionic acid | RC |
| 133 | 1 | methyl | oxo-phenyl | RC, RS, RW |
| 134 | 2 | methyl | oxo-phenyl | RW |
| 135 | 0 | H | 2,3,6-trimethyl-phenyl | RS |
| 136 | 0 | H | 2-nitrophenyl | RC, RW |
| 137 | 0 | H | 4-(2,2-dichloro-cyclopropyl)phenyl | RW |
| 138 | 2 | H | 2,3,6-trimethyl-phenyl | STR, RT, RS, RW |
| 139 | 2 | methyl | 2,4,6-trimethyl-phenyl | RT |
| 140 | 2 | H | 2-nitrophenyl | STR, RT, SSB |
| 141 | 1 | H | 2-nitrophenyl | STR, RT, RW, RS |
| 142 | 1 | H | 2,3,6-trimethyl-phenyl | RT, RW |
| 143 | 2 | H | 2-methyl(1-naphthyl) | RW |
| 144 | 1 | H | 2-methyl-(1-naphthyl) | RT |
| 145 | 1 | phenyl | 2-methylphenyl | RW |
| 146 | 2 | H | 1-iodophenyl | RS, RW |
| 147 | 1 | H | 1-iodophenyl | RT, RW, RS |
| 148 | 2 | methyl | 4-nitrophenyl | RT, RW |
| 149 | 2 | H | 4(2,2-dichloro-cyclopropyl)phenyl | RT |
| 150 | 1 | H | 4(2,2-dichloro-cyclopropyl)phenyl | RT, RS |
| 151 | 2 | methyl | 1-naphthyl | RT, RW |
| 152 | 1 | methyl | 1-naphthyl | RW |
| 153 | 0 | H | 3,4-dimethoxyphenyl | RT, RW |
| 154 | 1 | H | 3,4-dimethoxyphenyl | RW, RS |
| 155 | 2 | H | 3,4-dmethoxyphenyl | RW, RS |
| 156 | 2 | methyl | 2,5-diethylphenyl | RW, RW |
| 157 | 0 | methyl | 2,5-diisopropyl-phenyl | RS |
| 158 | 1 | cyclopentyl | | RT |
| 159 | 2 | cyclopentyl | | RT |
| 160 | 2 | H | 2,5-dimethoxyphenyl | RT, RS, RW |
| 161 | 1 | H | 2,5-dimethoxyphenyl | RS, RW |
| 162 | 1 | H | 2-ethoxyphenyl | RS |
| 163 | 2 | H | 2-ethoxyphenyl | RW, RS |
| 164 | 0 | methyl | 2-chloro-4-methyl-phenyl | RS |
| 165 | 2 | methyl | 2-chloro-4-methyl-phenyl | RS, RW |
| 166 | 1 | methyl | 2-chloro-4-methyl-phenyl | RS, RW |
| 167 | 0 | methyl | 2-chloro-5-methyl-phenyl | RT |
| 168 | 2 | methyl | 2,5-diisopropyl-phenyl | RT |
| 169 | 0 | H | 2,3,5,6-tetrachloro-4-methylphenyl | RT |
| 170 | 1 | H | 2,3,5,6-tetrachloro-4-methylphenyl | RT, RS, RW |
| 171 | 2 | H | 2,3,5,6-tetrachloro-4-methylphenyl | RT |
| 172 | 0 | methyl | 2,5-dichlorophenyl | RT |

TABLE II-continued
Plant Regulators

RW = retards wheat >30% 6000 ppm
RT = retards turf >50%/8.5#/A
RC = retards cotton >30%
RS = retards soybeans >30%
STR = stimulates turf roots >25%
SSB = stimulates sugar beets >25%
WT = wheat tillering
P = enhances production of soybeans >50%

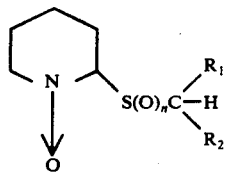

| No. | n | $R_1$ | $R_2$ | Activity |
|---|---|---|---|---|
| 173 | 1 | methyl | 2-chloro-5-methyl-phenyl | RS, RW |
| 174 | 2 | methyl | 2-chloro-5-methyl-phenyl | RS, RW |
| 175 | 1 | methyl | 2,5-dichlorophenyl | RT, RW |
| 176 | 2 | methyl | 2,5-dichlorophenyl | RT, RW, RS |
| 177 | 1 | methyl | 2,4,5-trimethyl-phenyl | RW, RT |
| 178 | 2 | methyl | 2,4,5-trimethyl-phenyl | RS, RW, RT |
| 179 | 1 | methyl | 2,3,4-trimethyl-phenyl | RC, RW, RT |
| 180 | 2 | methyl | 2,3,4-trimethyl-phenyl | RC, RW, RT |
| 181 | 1 | methyl | 2,3,4,5-tetramethyl-phenyl | RT |
| 182 | 2 | methyl | 2,3,4,5-tetramethyl-phenyl | RC, RW, RS, RT |
| 183 | 1 | H | 3,4,5-trimethoxy-phenyl | RC, RS |
| 184 | 2 | H | 3,4,5-trimethoxy-phenyl | RT |
| 185 | 1 | H | 9-anthryl | RT |
| 186 | 0 | H | 2-thienyl | RC |
| 187 | 1 | H | 2-thienyl | RS, RW |
| 188 | 2 | H | 2-thienyl | RC, RS, RW |
| 189 | 1 | methyl | phenyl | RT, RW |
| 190 | 1 | methyl | 2,5-dimethylphenyl | RT, RC, RW |
| 191 | 1 | methyl | 4-chlorophenyl | RT, RC, RW |
| 192 | 2 | methyl | 2,4-dichloro-3-methylphenyl | RC, RW |
| 193 | 1 | methyl | 2,4-dichloro-3-methylphenyl | RW |
| 194 | 0 | methyl | benzyl | RC |
| 195 | 2 | isobutyl | 2,5-dimethylphenyl | RT |
| 196 | 2 | methyl | benzyl | RT |
| 197 | 1 | methyl | benzyl | RT |
| 198 | 0 | methyl | 2,5-dichlorothienyl | RT |
| 199 | 0 | benzyl | 2,5-dimethylphenyl | RC |
| 200 | 0 | H | 4-vinylphenyl | RW |
| 201 | 1 | H | 4-vinylphenyl | RW, RS |
| 202 | 0 | methyl | 4-biphenyl | RW |
| 203 | 0 | methyl | 4-phenoxyphenyl | RW |
| 204 | 2 | methyl | 4-phenoxyphenyl | RC |
| 205 | 0 | methyl | 2-methyl-5-iso-propylphenyl | RC |
| 206 | 2 | methyl | 2-methyl-5-iso-propylphenyl | RC, RW |
| 207 | 0 | methyl | 5-indanyl | RC, RW |
| 208 | 2 | methyl | 5-indanyl | RC |

Preferred compounds employed in the method of the invention are those of formula I above wherein
n is 0, 1 or 2
$R_1$ is hydrogen, methyl or n-heptyl
$R_2$ is phenyl or phenyl substituted with from 1 to 3 substituents which may be the same or different and are selected from the group consisting of methyl and chlorine.

Particularly preferred are the following:
Compound 35, 2-(1-phenylethylsulfonyl)pyridine N-oxide, especially for use on turf and legumes such as soybeans.

Compound 109, 2-[1-(2,5-dimethylphenyl)ethylsulfonyl]pyridine N-oxide, especially for use on turf.

Compound 42, 2-(2,6-dichlorophenylmethylsulfinyl)-pyridine N-oxide, especially for use on legumes such as soybeans, cotton, peanuts, and sugar-producing species such as sugar beets.

Compound 50, 2-(2,5-dimethylphenylmethylsulfinyl)-pyridine N-oxide, especially for use on legumes such as soybeans.

Compound 57, 2-(2,4-dichlorophenylmethylsulfinyl)-pyridine N-oxide, especially for use on legumes such as soybeans.

Compound 83, 2-(2,3,6-trichlorophenylmethylthio)-pyridine N-oxide, especially for use on legumes such as soybeans.

Compound 115, 2-(1-[2,5-dimethylphenyl]octylthio) pyridine N-oxide, especially for use on sugar-producing species such as sugar beets.

New compounds of formula II above that are particularly remarkable for their unusual activity are:

| No. | |
|---|---|
| 80 | 2-(1-phenylbutylthio)pyridine N-oxide |
| 115 | 2-(1-[2,5-dimethylphenyl]octylthio)pyridine N-oxide |
| 122 | 2-(1-[2,5-dimethylphenyl]dodecylthio)pyridine N-oxide |

The following examples will serve to illustrate the practice of the invention in more detail.

EXAMPLE I

Turf

The test solutions are prepared by dissolving 10 milligram samples in acetone followed by dilution to 100 ml with water and two drops of "Tween 20"(trademark; polyoxyethylene sorbitan monooleate). The solutions are equivalent to 8.5 pounds per acre/100 ml which could be subsequently diluted o 4.25 and 2.12 pounds per acre equivalents.

A. The turf grass species are grown in three inch styrofoam cups 6 inches deep. The grass is planted and held in the cups until a good root system develops to fill the cup. The test solution of the desired concentration is then poured on the soil surface as a drench. About 1 week later the turf is clipped back to a uniform height. Percent growth inhibition is calculated by Abbotts formula compared to regrowth of untreated controls.

B. To observe root growth and top growth simultaneously a 3 inch black plastic pipe 12 inches long was cut longitudinally to a length of 11 inches to permit removal of a half section. A piece of copper screening was cemented to the bottom to confine the soil. The removable section was secured with a plastic strap.

The experiments are carried out by removing a treated plug from its styrofoam cup and inserting it into the tube containing eight inches of untreated soil. The tubes are placed in racks at a 45° angle on a greenhouse bench with the removable section down to permit the roots to grow along its surface. The tops are clipped 1 week after treatment and regrowth is measured at the same time as root observations are made.

the following table illustrates the results obtained from typical experiments.

|  | % TOP GROWTH INHIBITION | | | | | % ROOT GROWTH INHIBITION* | | | | | |
|---|---|---|---|---|---|---|---|---|---|---|---|
| Compound No. | Rye | St. Aug | Blue-Fesc | Bermuda | Ave. | Rye | St. Aug | Blue-Fesc | Bermuda | Avg. | Leaf Color |
| 109 | 93 | 100 | 100 | 100 | 98 | 0 | 0 | −50 | 0 | −13 | Good |
| 139 | 73 | 100 | 100 | 75 | 87 | 0 | 0 | +50 | 0 | +13 | Good |
| 35 | 87 | 78 | 79 | 100 | 86 | 0 | 0 | −35 | 0 | −9 | Good |
| 79 | 93 | 100 | 100 | 25 | 80 | −10 | 0 | 0 | +25 | +4 | Good |
| 68 | 47 | 56 | 86 | 83 | 68 | 0 | −50 | 0 | −50 | −25 | Good |
| Maleic Hydrazide | 80 | 67 | 75 | 79 | 75 | 100 | 100 | 100 | 100 | 100 | Poor |

Dosage 2.12 pounds/acre
*−inhibition
+stimulated.

EXAMPLE II

Cotton

The test solutions are prepared by dissolving 0.3 gm of compound in 10 ml of acetone and diluting to 100 ml with water containing 0.3% "Triton X100"(trademark; isooctylphenyl polyethoxy ethanol). Dilution to 200 ml yields solutions of 1500 ppm.

Cotton plants are grown in 6 inch pots to a height of 12 inches. Replicated plants are then sprayed to the drip point at dosages of 3000 and 1500 ppm. Height measurements are made two months after treatment.

The following table illustrates typical results obtained by the treatments.

| Compound No. | Dosage ppm | % Height Reduction | |
|---|---|---|---|
| 42 | 1500 | 50 | 2-(2,6-dichlorophenyl-methylsulfinyl)pyridine N-oxide |
|  | 3000 | 45 | |
| 61 | 1500 | 7 | 2-(phenylmethylsulfinyl) pyridine N-oxide |
|  | 3000 | 27 | |
| 121 | 1500 | 34 | 2-(3,4-dichlorophenyl-methylsulfinyl)pyridine N-oxide |
|  | 3000 | 36 | |
| 58 | 1500 | 34 | 2-(phenylethylsulfinyl) pyridine N-oxide |
|  | 3000 | 32 | |
| 10 | 1500 | 22 | 2-(4-chlorophenylmethyl-thio)pyridine N-oxide |
|  | 3000 | 37 | |
| 60 | 1500 | 44 | 2-(4-methoxyphenylmethyl-sulfinyl)pyridine N-oxide |
|  | 3000 | 32 | |

EXAMPLE III

Soybeans

The test solutions are prepared by weighing out 0.3 gm of test compound and dissolving in 10 ml of acetone. Dilution with water containing 125 ppm of "Tween 20"to 800 ml gave a test solution of 375 ppm.

Corsoy variety of soybeans are grown in 6 inch pots containing 2 plants per pot. When the plants are in the trifoliate stage replicates were sprayed to the drip point. Approximately 1 month later the number of pods per plant are counted and compared with the controls.

The following table illustrates typical results obtained.

| Compound No. | Average number pods/plant | % Increase |
|---|---|---|
| 57 | 11.0 | 134 |
| 83 | 10.7 | 128 |
| 96 | 10.0 | 113 |
| 67 | 9.3 | 98 |
| Untreated controls Dosage at 375 pm | 4.7 | — |

EXAMPLE IV

Wheat

The test solutions are made up by weighing out the compound and dissolving in 10 ml of acetone followed by dilution in water to give equivalents of 4 to 6 pounds/acre.

Waldron wheat is grown in 6 inch pots with three plants per pot. When the plant has reached the early boot stage the solution is poured into the saucer. The soil completely absorbs the liquid by this treatment. After 3 months the mature wheat was measured and the number of heads per plant counted.

The following table illustrates results obtained from these tests.

| Compound No. | Dosage lb/acre | % Retardation | Avg. No. mature heads/plant |
|---|---|---|---|
| 6 | 4 | 10 | 5.4 |
|   | 6 | 9 | 6.7 |
| 14 | 4 | 51 | 4.3 |
|   | 6 | 58 | 3.4 |
| Untreated | — | — | 3.0 |

EXAMPLE V

Sugarbeets

The test solutions are prepared by dissolving the weighed compound in 10 ml of acetone followed by dilution to 100 ml with water containing 2 drops of "Tween 20".

Sugarbeets are planted in 6 inch pots in the greenhouse at one per pot. When the tops become five inches tall and possess 16 leaves a soil drench is applied to replicates at rates of 1 to 2 pounds per acre. Approximately 3 months later the roots are freed from soil, weighed and compared to controls.

The following table illustrates results obtained.

| Example | Dosage #/acre | Avg. % increase in beet root weight over controls |
|---|---|---|
| 68 | 2 | 124 |
| 140 | 2 | 105 |
| 131 | 1 | 117 |
| 115 | 1 | 76 |

EXAMPLE VI

Peanuts

The major production of peanuts in the United States is with runner types. Each branch from the main stem produces a flower at each node, starting at the main stem. The flower then produces a peg which penetrates the soil to form the peanut pod. This is a continuous process until harvest. Pods formed during the latter part of the summer do not mature by harvest time. It is desirable to reduce number of pods formed so that those already formed will mature to maximum size.

To demonstrate the ability of the present compounds to reduce pod formation on runner type peanuts the following emulsifiable concentrate was prepared:

| 2-(2,6-dichlorophenylmethyl-sulfinyl) pyridine N-oxide | 12 grams |
|---|---|
| emulsifying agent | 10 grams |
| ethylene dichloride to | 100 ml |
|  | 122.39 grams. |

The emulsifying agent was a nonionic-anionic blend of alkyl phenoxy polyethoxy ethanols and organic sulfonates (Emulsifier AH861[trademark], Rohm & Haas); the concentration of the invention compound was 1.0 pound per gallon.

Florigiant variety of Virginia type runner peanuts (*Arachis hypogaea* L.) were planted in deep flats, four plants per flat; 74 days later they were sprayed to runoff with formulations made by diluting the above concentrate to 1250 and 2500 ppm. Seven weeks later the plants were harvested and the number of pods and pegs on each node were counted. The following table summarizes the data. It is apparent that the number of pods and pegs were reduced by the treatment.

| | | Total Number of Pods and Pegs on Four Peanut Plants | | | | | | | | | | |
|---|---|---|---|---|---|---|---|---|---|---|---|---|
| | | Node Number | | | | | | | | | | |
| | | 1 | 2 | 3 | 4 | 5 | 6 | 7 | 8 | 9 | 10 | Total |
| Check | pods | 26 | 20 | 18 | 10 | 3 | 1 | 0 | 0 | 0 | 0 | 78 |
| | pegs | 5 | 13 | 9 | 7 | 11 | 8 | 7 | 2 | 7 | 1 | 70 |
| | | | | | | | | | | | | 148 |
| Treatment 1250 ppm | pods | 15 | 22 | 11 | 1 | 1 | 3 | 0 | | | | 53 |
| | pegs | 4 | 4 | 1 | 1 | 0 | 3 | 2 | | | | 15 |
| | | | | | | | | | | | | 68 |
| Treatment 2500 ppm | pods | 22 | 14 | 5 | 1 | 0 | 2 | | | | | 44 |
| | pegs | 4 | 5 | 8 | 1 | 1 | 0 | | | | | 19 |
| | | | | | | | | | | | | 63 |

We claim:

1. A method of regulating the natural growth or development of plants which comprises applying to said plants an effective non-herbicidal plant-regulating amount of a 2-sulfinyl-, or 2-sulfonyl-pyridine N-oxide compound of the formula

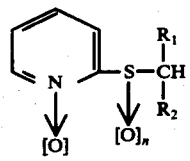

wherein:
$n$ is 1 or 2;
$R_1$ is hydrogen, $C_1$ to $C_{15}$ alkyl, phenyl or benzyl;
$R_2$ is hydrogen,
$C_1$ to $C_{12}$ alkyl,
$C_1$ to $C_4$ alkenyl,
$C_2$ or $C_3$ alkoxycarbonyl,
$C_5$ or $C_6$ alicyclic,
phenyl provided $R_1$ is not phenyl,
phenyl substituted with from 1 to 3 substituents which may be the same or different and are selected from the group consisting of $C_1$ to $C_3$ alkyl, halogen, cyano, nitro, $C_1$ or $C_2$ alkoxy, phenoxy, dioxymethylene and 2,2-dichlorocyclopropyl; and phenyl substituted with 4 to 5 substituents which may be the same or different and are selected from methyl and chlorine;
1-methyl-2,2-dichlorocyclopropyl,
2,2-dichlorocyclopropyl,
naphthyl, 9-anthryl, 5-indanyl,
4-biphenylyl,
2-benzothiazolyl, 2-thienyl or benzyl;
$R_1$ and $R_2$ may be joined together in the form of a polymethylene chain $—(CH_2)_m-$ where $m$ is 3,4 or 5 to form a carbocyclic ring;
and when $R_1$ is hydrogen or methyl $R_2$ can be the radical

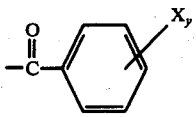

where y is 0, 1 or 2 and the X's are the same or different and are selected from $C_1$ to $C_3$ alkyl, halogen, and 2,2-dichlorocyclopropyl.

2. A method as in claim 1 in which
n is 1 or 2
$R_1$ is hydrogen, methyl or n-heptyl
$R_2$ is phenyl or phenyl substituted with 1 to 3 substituents which may be the same or different and are selected from the group consisting of methyl and chlorine.

3. A method as in claim 2 in which the said compound is applied to turf.

4. A method as in claim 2 in which the said compound is applied to soybeans.

5. A method as in claim 2 in which the said compound is applied to cotton.

6. A method as in claim 2 in which the said compound is applied to sugar beets.

7. A method as in claim 2 in which the said compound is applied to peanuts.

8. A method as in claim 1 in which the said compound is applied to turf, and the said compound is selected from the group consisting of
2-(1-[2,5-dimethylphenyl]ethylsulfonyl) pyridine N-oxide
2-(1-phenylethylsulfonyl)pyridine N-oxide
2-(1-[4-methylphenyl]ethylsulfonyl)pyridine N-oxide
2-(2,6-dichlorophenylmethylsulfinyl)pyridine N-oxide
2-(1-[2,4,6-trimethylphenyl]ethylsulfonyl)-pyridine N-oxide
2-(2,4,6-trimethylphenylmethylsulfonyl)pyridine N-oxide
2-(1-[2-chlorophenyl]ethylsulfonyl)pyridine N-oxide
2-(2,5-dimethylphenylmethylsulfonyl)pyridine N-oxide
2-(2,4-dichlorophenylmethylsulfinyl)pyridine N-oxide
2-(2,3,6-trimethylphenylmethylsulfonyl)pyridine N-oxide
2-(3,4-dimethylphenylmethylsulfonyl)pyridine N-oxide
2-(2-methylphenylmethylsulfinyl)pyridine N-oxide
2-(2-methylphenylmethylsulfonyl)pyridine N-oxide
2-(2,3,6-trimethylphenylmethylsulfinyl)pyridine N-oxide and
2-(2-oxo-2-[2,5-dimethylphenyl]ethylsulfinyl)pyridine N-oxide.

9. A method as in claim 8 in which the said compound is 2-(1-phenylethylsulfonyl)pyridine N-oxide or 2-(1-[2,5-dimethylphenyl]ethylsulfonyl)pyridine N-oxide.

10. A method as in claim 1 in which the said compound is applied to wheat, and the said compound is selected from the group consisting of
2-(2,5-dimethylphenylmethylsulfonyl)pyridine N-oxide
2-(3,4-dimethylphenylmethylsulfonyl)pyridine N-oxide and
2-(1-[2,5-dimethylphenyl]ethylsulfonyl)pyridine N-oxide.

11. A method as in claim 1 in which the said compound is applied to sugar beets, and the said compound is selected from the group consisting of
2-(2,6-dichlorophenylmethylsulfinyl)pyridine N-oxide
2-(2-methylphenylmethylsulfinyl)pyridine N-oxide
2-(2-oxo-2-[2,5-diisopropylphenyl]ethylsulfinyl)pyridine N-oxide.
2-(2-nitrophenylmethylsulfonyl)pyridine N-oxide.

12. A method as in claim 11 in which the said compound is
2-(2,6-dichlorophenylmethylsulfinyl)pyridine N-oxide.

13. A method as in claim 1 in which the said compound is applied to soybeans, and the said compound is selected from the group consisting of
2-(1-phenylethylsulfonyl)pyridine N-oxide
2-(2,6-dichlorophenylmethylsulfinyl)pyridine N-oxide
2-(2-fluorophenylmethylsulfinyl)pyridine N-oxide
2-(2-methylphenylmethylsulfinyl)pyridine N-oxide
2-(2-methylphenylmethylsulfonyl)pyridine N-oxide
2-(4-cyanophenylmethylsulfinyl)pyridine N-oxide
2-(2,4-dichlorophenylmethylsulfinyl)pyridine N-oxide
2-(2,5-dimethylphenylmethylsulfinyl)pyridine N-oxide
2-(3,4-dimethylphenylmethylsulfinyl)pyridine N-oxide
2-(1-[4-chlorophenyl]ethylsulfonyl)pyridine N-oxide
2-(1-[2-naphthyl]ethylsulfonyl)pyridine N-oxide and
2-(2-oxo-2-[2,5-dimethylphenyl]ethylsulfinyl)pyridine N-oxide.

14. A method as in claim 13 in which the said compound is
2-(1-phenylethylsulfonyl)pyridine N-oxide
2-(2,6-dichlorophenylmethylsulfinyl)pyridine N-oxide
2-(2,4-dichlorophenylmethylsulfinyl)pyridine N-oxide
2-(2,5-dimethylphenylmethylsulfinyl)pyridine N-oxide.

15. A method as in claim 1 in which the said compound is applied to cotton, and the said compound is selected from the group consisting of
2-(phenylmethylsulfinyl)pyridine N-oxide
2-(3-methylphenylmethylsulfinyl)pyridine N-oxide
2-(4-methoxyphenylmethylsulfinyl)pyridine N-oxide
2-(2,6-dichlorophenylmethylsulfinyl)pyridine N-oxide
2-(3,4-dichlorophenylmethylsulfinyl)pyridine N-oxide
2-(1-[2,5-dimethylphenyl]ethylsulfonyl)pyridine N-oxide
2-(2-phenylethylsulfinyl)pyridine N-oxide.

16. A method as in claim 15 in which the said compound is
2-(2,6-dichlorophenylmethylsulfinyl)pyridine N-oxide.

17. A method as in claim 1 in which the said compound is applied to peanuts and the said compound is
2-(2,6-dichlorophenylmethylsulfinyl)pyridine N-oxide.

18. A method as in claim 1 in which the said compound is
2-(1-phenylethylsulfonyl)pyridine N-oxide.

19. A method as in claim 1 in which the said compound is

2-[1-(2,5-dimethylphenyl)ethylsulfonyl]pyridine N-oxide.

20. A method as in claim 1 in which the said compound is
2-(2,6-dichlorophenylmethylsulfinyl)pyridine N-oxide.

21. A method as in claim 1 in which the said compound is
2-(2,5-dimethylphenylmethylsulfinyl)pyridine N-oxide.

22. A method as in claim 1 in which the said compound is
2-(2,4-dichlorophenylmethylsulfinyl)pyridine N-oxide.

* * * * *